US011751995B2

(12) United States Patent
Huddleston

(10) Patent No.: US 11,751,995 B2
(45) Date of Patent: Sep. 12, 2023

(54) APPARATUS AND METHODS FOR MINIMALLY INVASIVE TRANSAPICAL ACCESS

(71) Applicant: Tendyne Holdings, Inc., St. Paul, MN (US)

(72) Inventor: Preston James Huddleston, Maplewood, MN (US)

(73) Assignee: Tendyne Holdings, Inc., St. Paul, MN (US)

( * ) Notice: Subject to any disclaimer, the term of this patent is extended or adjusted under 35 U.S.C. 154(b) by 222 days.

(21) Appl. No.: 17/194,378

(22) Filed: Mar. 8, 2021

(65) Prior Publication Data

US 2021/0298899 A1 Sep. 30, 2021

Related U.S. Application Data

(60) Provisional application No. 63/001,593, filed on Mar. 30, 2020.

(51) Int. Cl.
*A61F 2/24* (2006.01)
*A61B 17/34* (2006.01)

(52) U.S. Cl.
CPC ........ *A61F 2/2433* (2013.01); *A61B 17/3468* (2013.01)

(58) Field of Classification Search
CPC ........ A61F 2/24–2496; A61B 17/3468; A61M 29/00–2029/025
See application file for complete search history.

(56) References Cited

U.S. PATENT DOCUMENTS

| 4,762,128 | A * | 8/1988 | Rosenbluth | A61F 2/958 |
| | | | | 604/103.08 |
| 4,913,139 | A * | 4/1990 | Ballew | A61M 16/0488 |
| | | | | 128/207.14 |
| 10,327,894 | B2 * | 6/2019 | Vidlund | A61F 2/2418 |
| 11,160,956 | B1 * | 11/2021 | Hoganson | A61B 17/3494 |
| 11,337,802 | B2 * | 5/2022 | Hariton | A61F 2/2454 |
| 11,389,195 | B2 * | 7/2022 | Marshall | A61B 17/3417 |
| 2004/0049211 | A1 * | 3/2004 | Tremulis | A61F 2/2487 |
| | | | | 623/1.36 |

(Continued)

FOREIGN PATENT DOCUMENTS

| AU | 2014233505 B2 | 9/2019 |
| EP | 1189654 B1 | 9/2004 |

OTHER PUBLICATIONS

European Search Report for Application No. EP 21165690.5, dated Sep. 8, 2021, 8 pages.

*Primary Examiner* — Tan-Uyen T Ho
*Assistant Examiner* — Charles M Wei
(74) *Attorney, Agent, or Firm* — SLEMAN & LUND LLP

(57) ABSTRACT

A delivery catheter system includes an anchor catheter, a collapsible and expandable anchor, a balloon catheter, and a needle. The anchor may be for anchoring a prosthetic heart valve in a native heart valve. The anchor may be configured to be received within the anchor catheter. The balloon catheter may be positioned radially inward of the anchor catheter, and may include an inflatable balloon at a distal end thereof. The balloon may be in fluid communication with the balloon catheter. The needle may be positioned radially inward of the balloon catheter and may be translatable relative to the balloon, the needle having a sharp distal tip.

9 Claims, 30 Drawing Sheets

(56) References Cited

U.S. PATENT DOCUMENTS

| | | | |
|---|---|---|---|
| 2005/0075723 A1* | 4/2005 | Schroeder | A61F 2/2487 623/2.1 |
| 2006/0229708 A1* | 10/2006 | Powell | A61B 17/0401 623/1.24 |
| 2010/0298929 A1* | 11/2010 | Thornton | A61F 2/246 623/2.1 |
| 2014/0371846 A1* | 12/2014 | Wilson | A61F 2/246 623/2.11 |
| 2015/0196393 A1 | 7/2015 | Vidlund et al. | |
| 2015/0250590 A1 | 9/2015 | Gries et al. | |
| 2017/0079790 A1* | 3/2017 | Vidlund | A61B 17/0401 |
| 2017/0312078 A1* | 11/2017 | Krivoruchko | A61F 2/2457 |
| 2018/0078370 A1* | 3/2018 | Kovalsky | A61F 2/2433 |
| 2019/0083262 A1* | 3/2019 | Hariton | A61F 2/2454 |
| 2020/0188093 A1* | 6/2020 | Wang | A61F 2/2412 |
| 2021/0369257 A1* | 12/2021 | Huddleston | A61B 17/3478 |

* cited by examiner

APPARATUS AND METHODS FOR MINIMALLY INVASIVE TRANSAPICAL ACCESS

CROSS-REFERENCE TO RELATED APPLICATIONS

The present application claims the priority of the filing date of U.S. Provisional Patent Application No. 63/001,593, filed Mar. 30, 2020, the disclosure of which is hereby incorporated by reference herein.

BACKGROUND OF THE DISCLOSURE

Valvular heart disease, and specifically aortic and mitral valve disease, is a significant health issue in the United States. Valve replacement is one option for treating heart valves diseases. Traditional valve replacement surgery, the orthotopic replacement of a heart valve, is an "open heart" surgical procedure. Briefly, the procedure necessitates a surgical opening of the thorax, initiation of extra-corporeal circulation with a heart-lung machine, stopping and opening the heart, excision and replacement of the diseased valve, and re-starting of the heart. While valve replacement surgery typically carries a 1-4% mortality risk in otherwise healthy persons, a significantly higher morbidity is associated with the procedure, largely due to the necessity for extra-corporeal circulation. Further, open heart surgery is often poorly tolerated in elderly patients. Thus, if the extra-corporeal component of the procedure could be eliminated, morbidities and cost of valve replacement therapies would be significantly reduced.

While replacement of the aortic valve in a transcatheter manner is the subject of intense investigation, lesser attention has been focused on the mitral valve. This is in part reflective of the greater level of complexity associated with the native mitral valve and thus a greater level of difficulty with regard to inserting and anchoring the replacement prosthesis.

Recent developments in the field have provided devices and methods for mitral valve replacement with reduced invasion and risk to the patient. Such devices may include a prosthetic valve disposed within the native valve annulus and held in place with an anchor seated against an exterior surface of the heart near the ventricular apex, and such anchors must be at least a certain size to seat against the heart with adequate security. Methods of implanting such devices therefore typically require providing an intercostal puncture of significant size to accommodate the anchor. Trauma to the patient increases as a function of the diameter of the puncture. Accordingly, methods and devices for anchoring a prosthetic heart valve that avoid the need for an intercostal puncture would improve patient outcomes.

BRIEF SUMMARY OF THE DISCLOSURE

According to a first aspect of the disclosure, a delivery catheter system includes an anchor catheter, a collapsible and expandable anchor, a balloon catheter, and a needle. The anchor may be for anchoring a prosthetic heart valve in a native heart valve. The anchor may be configured to be received within the anchor catheter. The balloon catheter may be positioned radially inward of the anchor catheter, and may include an inflatable balloon at a distal end thereof. The balloon may be in fluid communication with the balloon catheter. The needle may be positioned radially inward of the balloon catheter and may be translatable relative to the balloon, the needle having a sharp distal tip.

According to another embodiment of the disclosure, a method of delivering an expandable prosthetic heart valve anchor to a heart of a patient includes positioning the anchor within an anchor catheter, the anchor catheter maintaining the anchor in a collapsed condition. The anchor catheter may be advanced to a right atrium of the heart of the patient, through a puncture in an atrial septum of the heart of the patient, and into a left atrium of the heart of the patient. The anchor catheter may be advanced from the left atrium of the heart of the patient to a left ventricle of the heart of the patient. A needle positioned radially within the anchor catheter may be advanced distally relative to the anchor catheter and through a ventricular wall of the heart of the patient to create a transapical puncture. The anchor catheter may be advanced at least partially through the transapical puncture. The anchor may be released from the anchor catheter and the anchor may be allowed to transition from the collapsed condition to an expanded condition while the anchor catheter is positioned at least partially through the transapical puncture.

DETAILED DESCRIPTION

As used herein, the term "proximal," when used in connection with a delivery device or components of a delivery device, refers to the end of the device closer to the user of the device when the device is being used as intended. On the other hand, the term "distal," when used in connection with a delivery device or components of a delivery device, refers to the end of the device farther away from the user when the device is being used as intended. As used herein, the terms "substantially," "generally," "approximately," and "about" are intended to mean that slight deviations from absolute are included within the scope of the term so modified.

Figure 1:
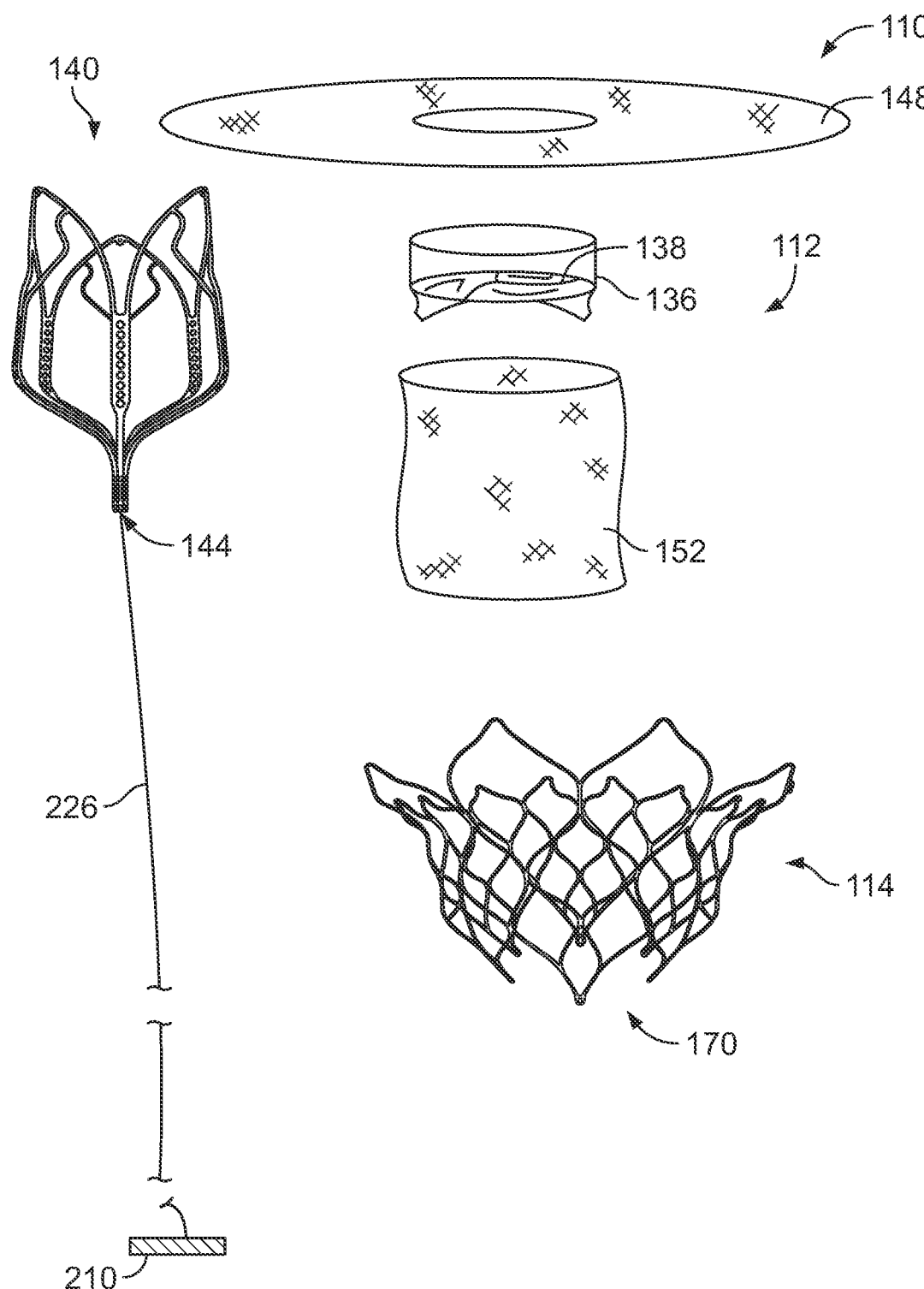
FIG. 1 is an exploded view of a prosthetic heart valve.

An exemplary prosthetic heart valve 110 as may be used with various embodiments of the present disclosure is shown in an exploded view in FIG. 1. Valve 110 includes an inner structure or assembly 112 and an outer structure or assembly 114. Valve 110 may be coupled to a tether 226 and a collapsible tether anchor 210.

Inner assembly 112 may include an inner frame 140, outer wrap 152 which may be cylindrical, and leaflet structure 136 (including articulating leaflets 138 that define a valve function). Leaflet structure 136 may be sewn to inner frame 140, and may use parts of inner frame 140 for this purpose, although method of attachment other than sutures may be suitable. Inner assembly 112 is disposed and secured within outer assembly 114, as described in more detail below.

Outer assembly 114 includes outer frame 170. Outer frame 170 may also have in various embodiments an outer frame cover of tissue or fabric (not pictured), or may be left without an outer cover to provide exposed wireframe to facilitate in-growth of tissue. Outer frame 170 may also have an articulating collar or cuff (not pictured) covered by a cover 148 of tissue or fabric.

Tether 226 is connected to valve 110 by inner frame 140. Thus, inner frame 140 includes tether connecting or clamping portion 144 by which inner frame 140, and by extension valve 110, is coupled to tether 226.

Figure 2:
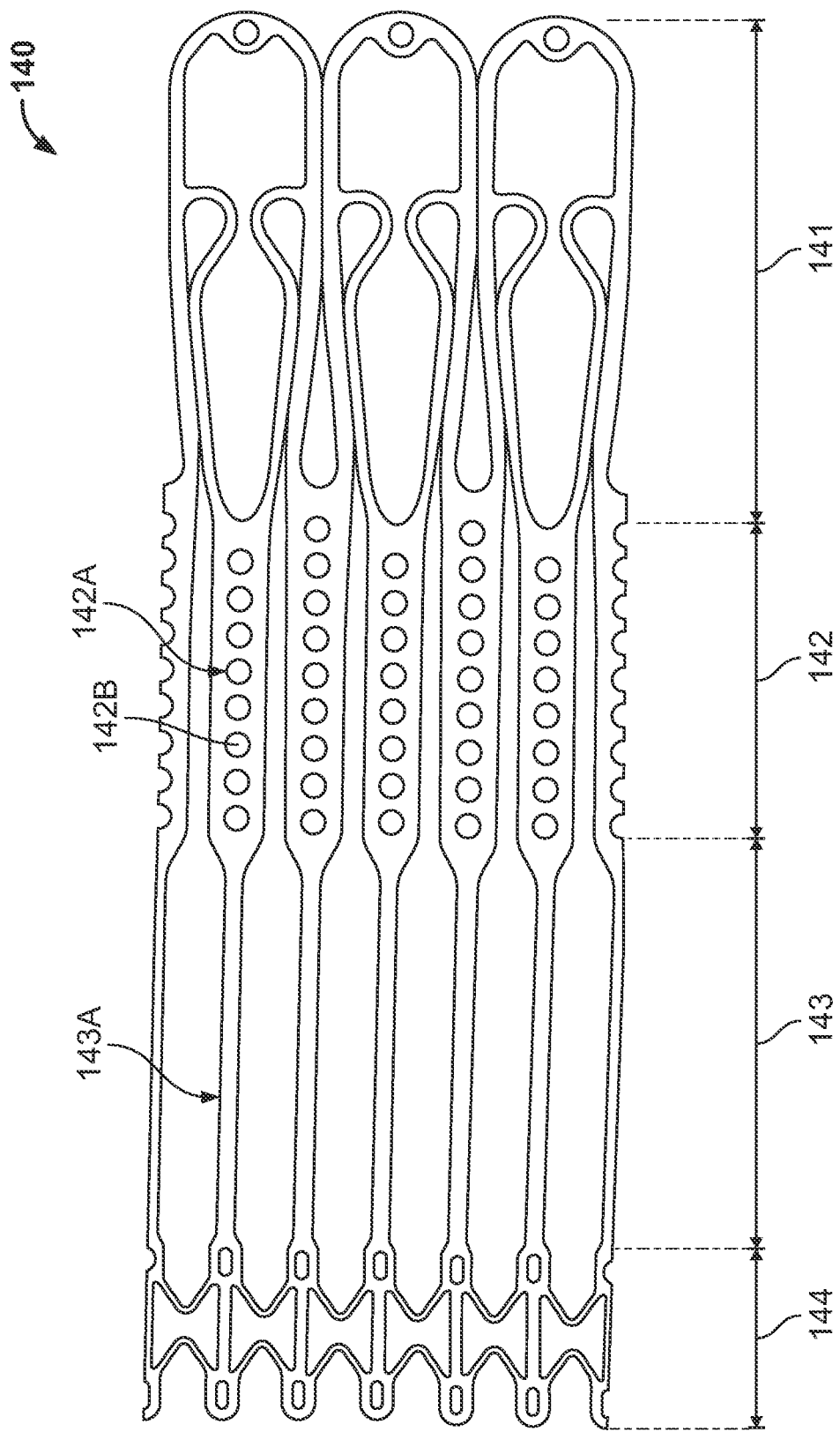
FIG. 2 is an opened and flattened view of an unexpanded inner frame of the prosthetic heart valve of FIG. 1.
Figure 3:
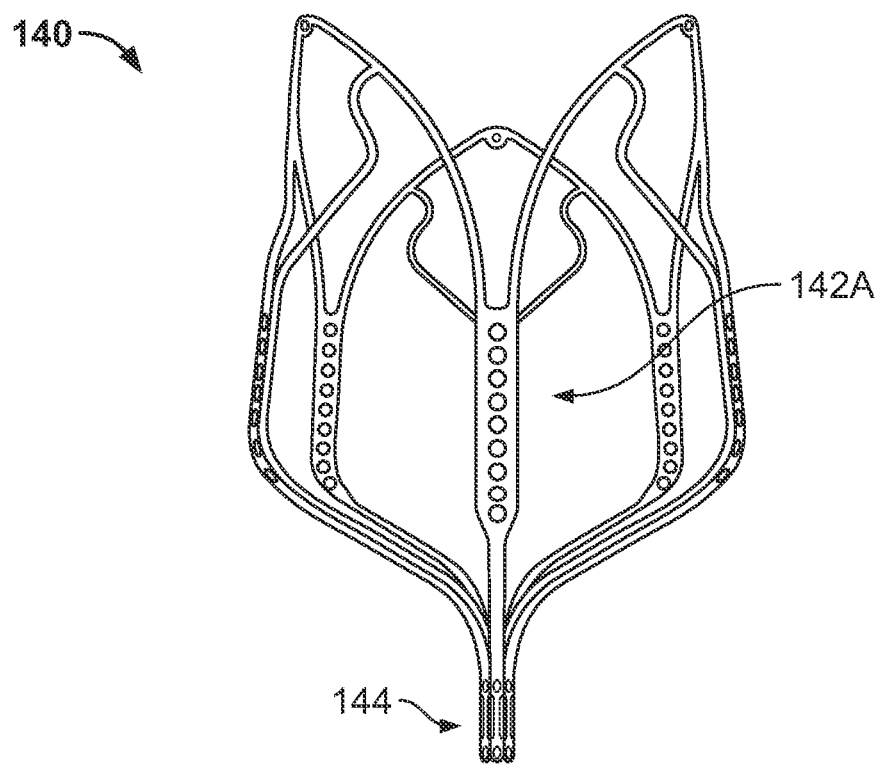
FIGS. 3 and 4 are side and bottom views, respectively, of the inner frame of FIG. 2 in an expanded configuration.
Figure 4:
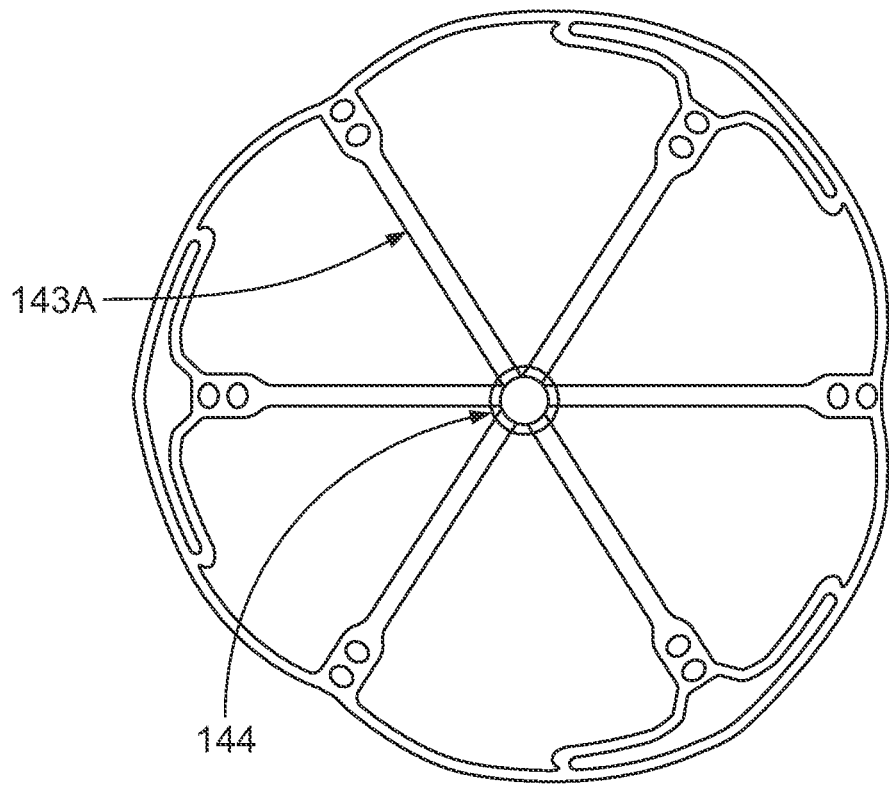

Inner frame 140 is shown in more detail in FIGS. 2-4. Inner frame 140 can be formed from a milled or laser-cut tube of a shape-memory material such as, for example, nitinol. Inner frame 140 is illustrated in FIG. 2 in an initial state, e.g., as milled or laser-cut, but cut longitudinally and unrolled into a flat sheet for ease of illustration. This initial state may generally correspond to a collapsed condition. Inner frame 140 is shown fully deformed, e.g., to the expanded, deployed configuration, in the side view and bottom view of FIGS. 3 and 4, respectively. Inner frame 140 can be divided into four portions corresponding to functionally different portions of inner frame 140 in final form: apex portion 141, body portion 142, strut portion 143, and tether connecting portion 144. Strut portion 143 includes six struts, such as strut 143A, which connect body portion 142 to connecting portion 144. A greater or lesser number of struts is contemplated herein.

Connecting portion 144 includes longitudinal extensions of the struts, connected circumferentially to one another by pairs of v-shaped connecting members, which may be referred to herein as "micro-V's." Connecting portion 144 is configured to be radially collapsed by application of a compressive force, which causes the micro-V's to become more deeply V-shaped, with each pair of vertices moving closer together longitudinally and the open ends of the V shapes moving closer together circumferentially. When collapsed, connecting portion 144 can clamp or grip one end of tether 226, either connecting directly onto a tether line (e.g., braided filament line) or onto an intermediate structure, such as a polymer or metal piece that is, in turn, firmly fixed to the tether line. The foregoing is merely exemplary and other techniques can be used to connect tether 226 to connecting portion 144.

In contrast to connecting portion 144, apex portion 141 and body portion 142 are configured to be expanded radially. Strut portion 143 forms a longitudinal connection, and radial transition, between the expanded body portion 142 and the compressed connecting portion 144.

Body portion 142 includes six longitudinal posts, such as post 142A, although the body portion may include a greater or lesser number of such posts. The posts can be used to attach leaflet structure 136 to inner frame 140, and/or can be used to attach inner assembly 112 to outer assembly 114, such as by connecting inner frame 140 to outer frame 170. In the illustrated example, posts 142A include apertures 142B through which connecting members (such as suture filaments and/or wires) can be passed to couple the posts to other structures.

Figure 5:
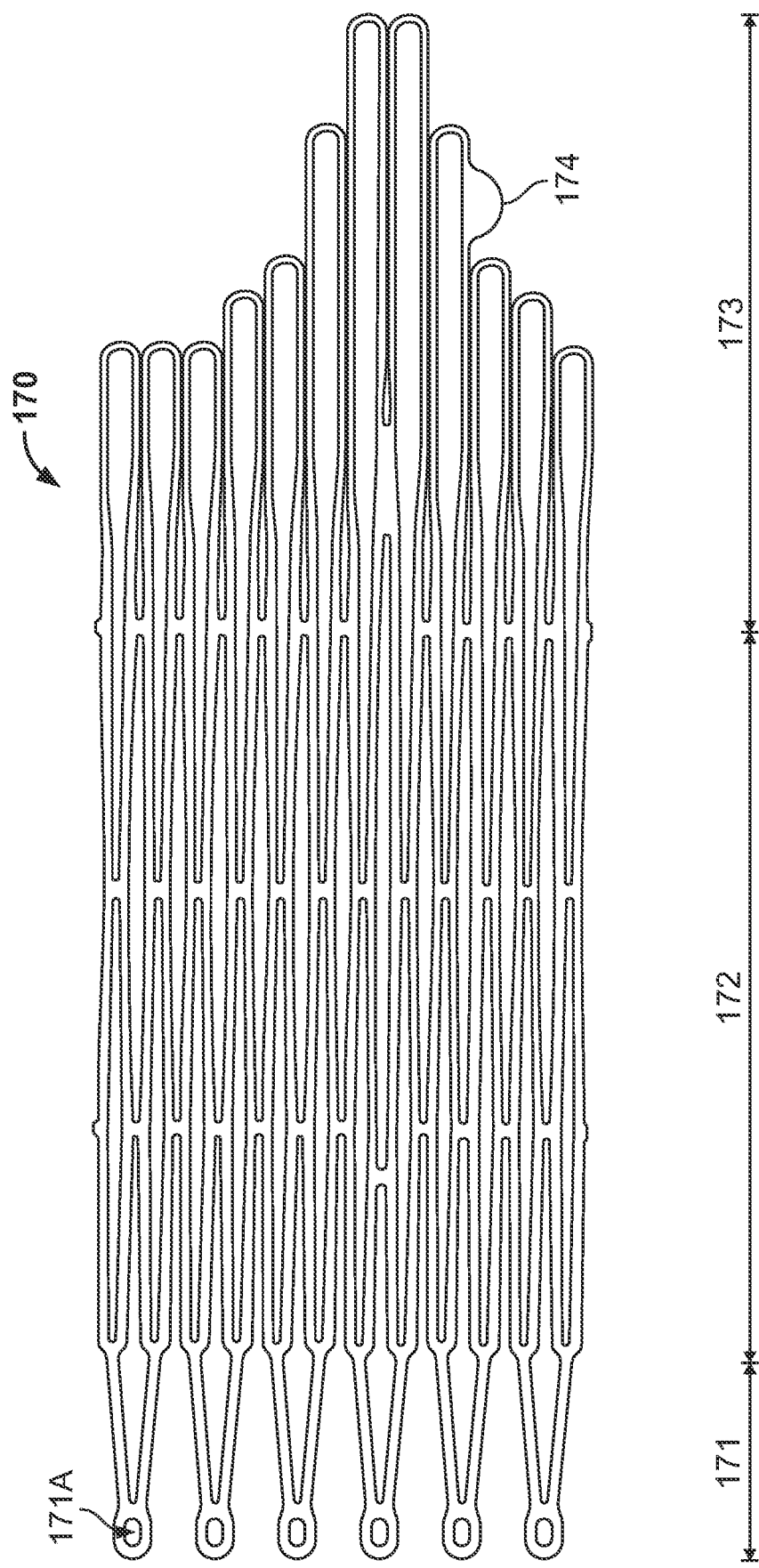
FIG. 5 is an opened and flattened view of an unexpanded outer frame of the prosthetic heart valve of FIG. 1.
Figure 6:
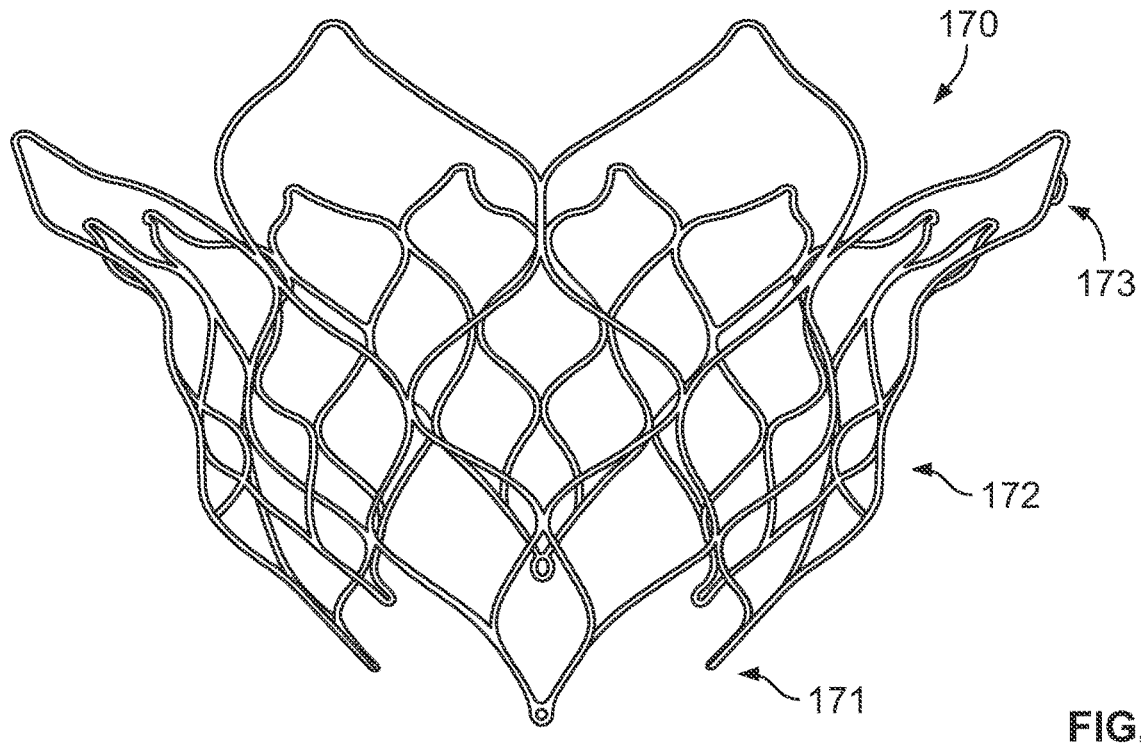
FIGS. 6 and 7 are side and top views, respectively, of the outer frame of FIG. 5 in an expanded configuration.
Figure 7:
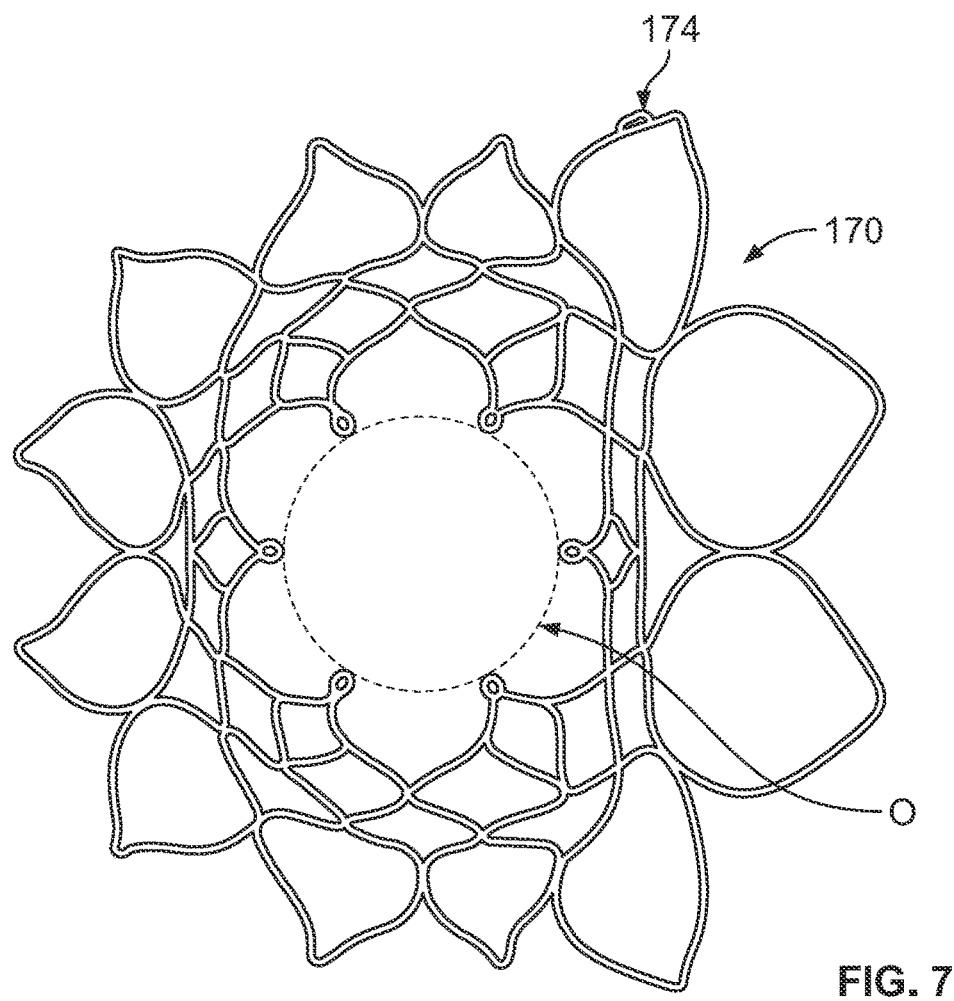

Outer frame 170 of valve 110 is shown in more detail in FIGS. 5-7. Outer frame 170 can be formed from a milled or laser-cut tube of a shape-memory material such as, for example, nitinol. Outer frame 170 is illustrated in FIG. 5 in an initial state, e.g., as milled or laser-cut, but cut longitudinally and unrolled into a flat sheet for ease of illustration. This initial state may generally correspond to the collapsed condition. Outer frame 170 can be divided into a coupling portion 171, a body portion 172, and a flared portion 173, as shown in FIG. 5. Coupling portion 171 may include multiple openings or apertures 171A by which outer frame 170 can be coupled to inner frame 140, as described in greater detail below.

Flared portion 173 may include an indicator 174. In one example, indicator 174 is simply a broader portion of the wire frame element of flared portion 173. Indicator 174 may be more apparent in radiographic or other imaging modalities than the surrounding wireframe elements of flared portion 173. In other examples, indicator 174 can be any distinguishable feature (e.g., protrusion, notch, etc.) and/or indicia (e.g., lines, markings, tic marks, etc.) that enhance the visibility of the part of flared portion 173 on which it is formed, or to which it is attached. Indicator 174 can facilitate the implantation of the prosthetic valve by providing a reference point or landmark that the operator can use to orient and/or position the valve (or any portion of the valve) with respect to the native valve annulus or other heart structure. For example, during implantation, an operator can identify (e.g., using echocardiography) indicator 174 when the valve 110 is situated in a patient's heart. The operator can therefore determine the location and/or orientation of the valve and make adjustments accordingly.

Outer frame 170 is shown in an expanded, deployed configuration, in the side view and top view of FIGS. 6 and 7, respectively. As best seen in FIG. 7, the lower end of coupling portion 171 may form a roughly circular opening (identified by "O" in FIG. 7). The diameter of this opening preferably corresponds approximately to the diameter of body portion 142 of inner frame 140, when the inner frame is in the expanded condition, to facilitate the coupling together of these two components of valve 110.

Figure 8:
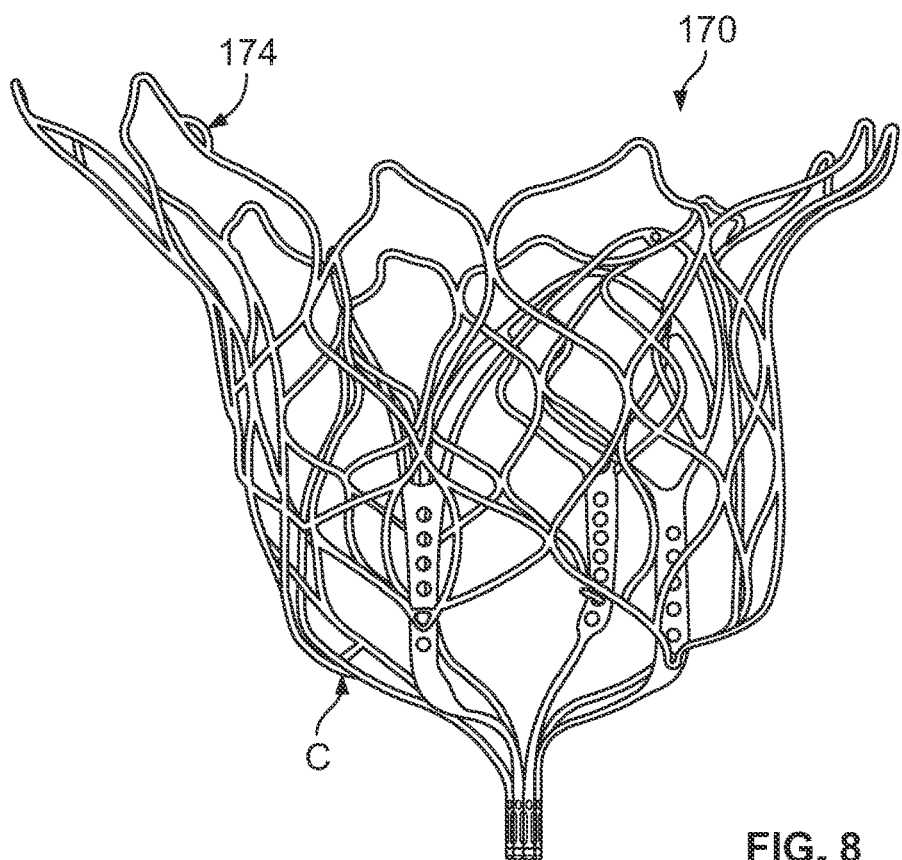
FIGS. 8-10 are side, front, and top views, respectively, of an assembly of the inner frame of FIGS. 2-4 and the outer frame of FIGS. 5-7, all in an expanded configuration.
Figure 9:
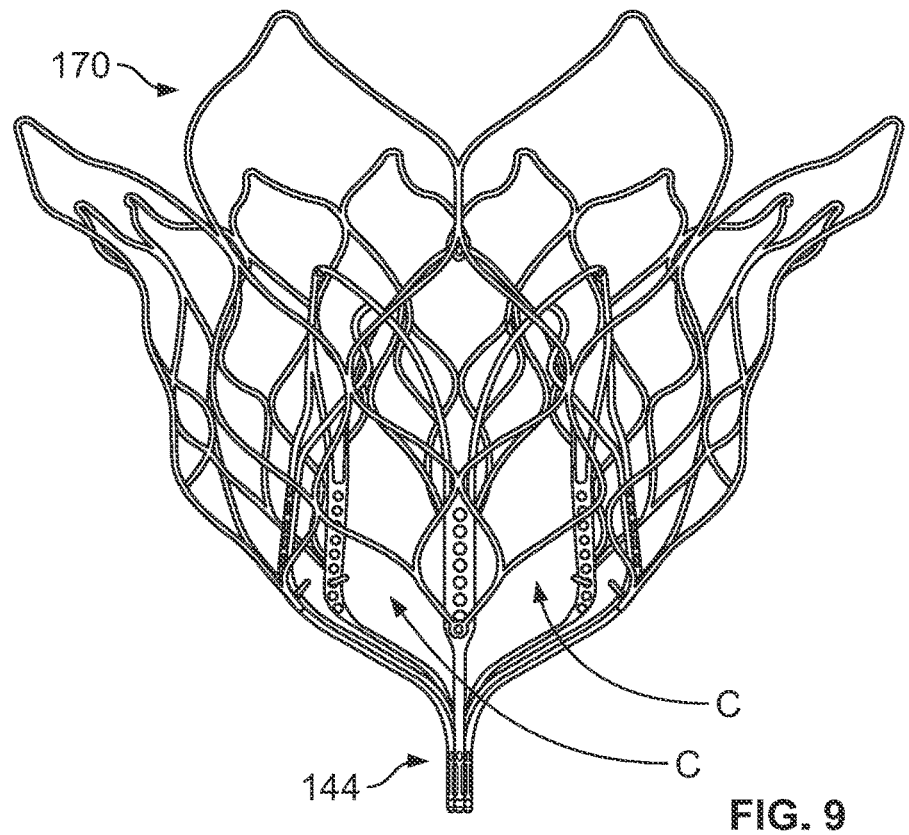
Figure 10:
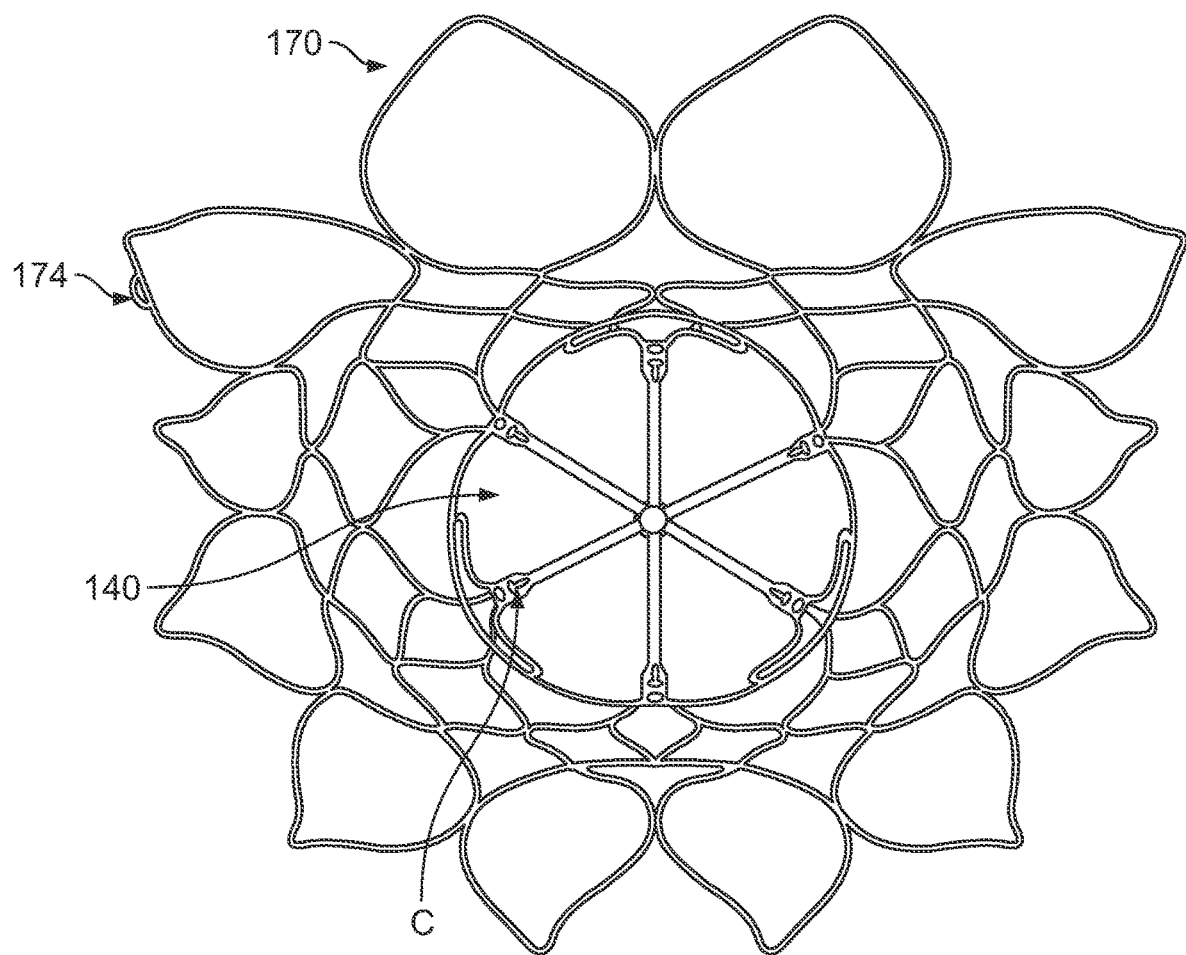

Outer frame 170 and inner frame 140 are shown coupled together in FIGS. 8-10 in front, side, and top views, respectively. The two frames collectively form a structural support for a valve leaflet structure, such as leaflet structure 136 in FIG. 1. The frames support leaflet structure 136 in the desired relationship to the native valve annulus, support the coverings for the two frames to provide a barrier to blood leakage between the atrium and ventricle, and couple to the tether 226 (by the inner frame 140) to aid in holding the prosthetic valve in place in the native valve annulus by the connection of the free end of the tether and tether anchor 210 to the ventricle wall, as described more fully below. The two frames are connected at six coupling points (representative points are identified as "C"). In this embodiment, the coupling of the frames is implemented with a mechanical fastener, such as a short length of wire, passed through an aperture 171A in coupling portion 171 of outer frame 170 and a corresponding aperture 142B in a longitudinal post 142A in body portion 142 of inner frame 140. Inner frame 140 is thus disposed within the outer frame 170 and securely coupled to it.

Figure 11A:
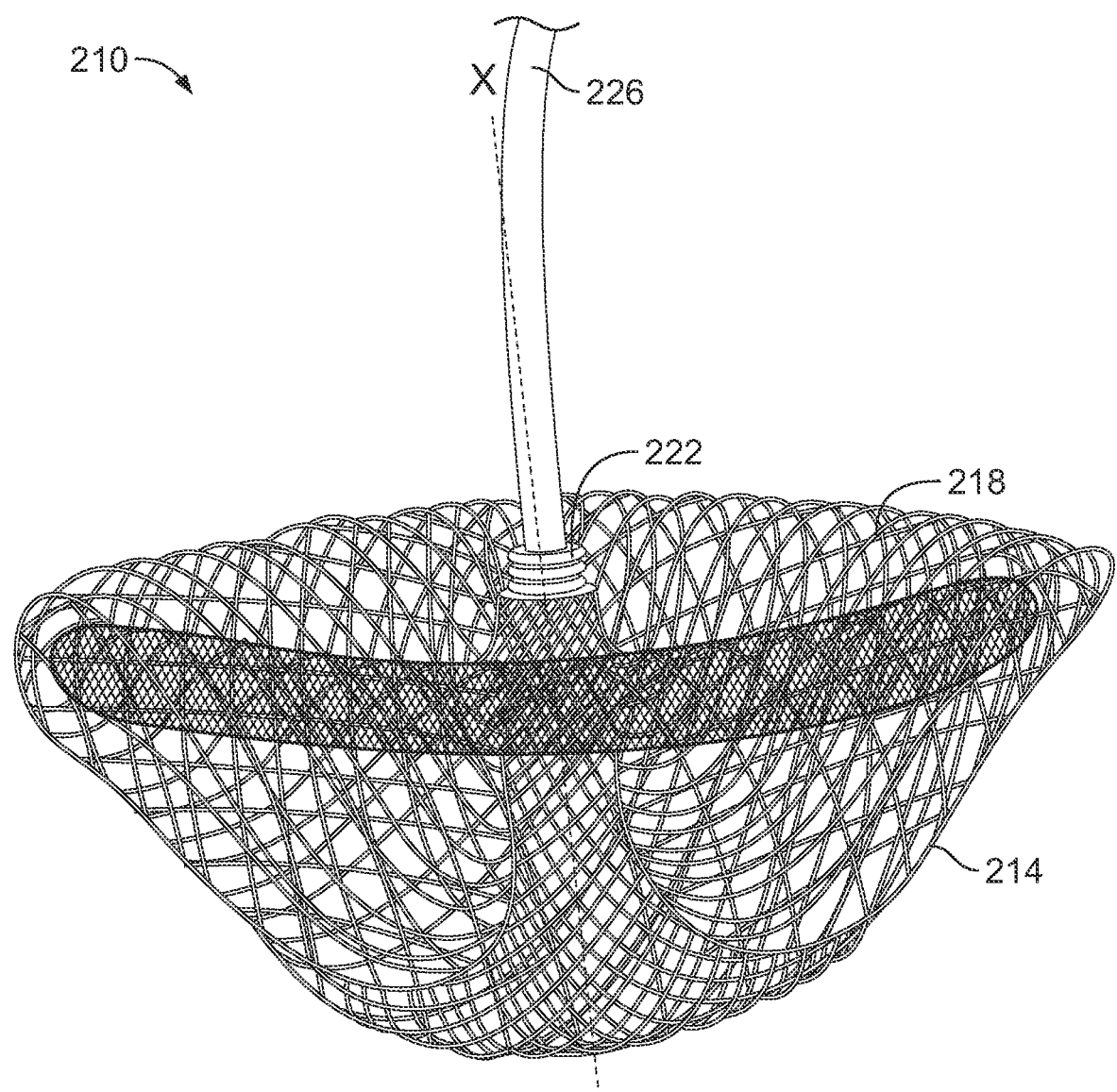
FIG. 11A is a perspective view of an anchor for the prosthetic valve of FIG. 1.
Figure 11B:
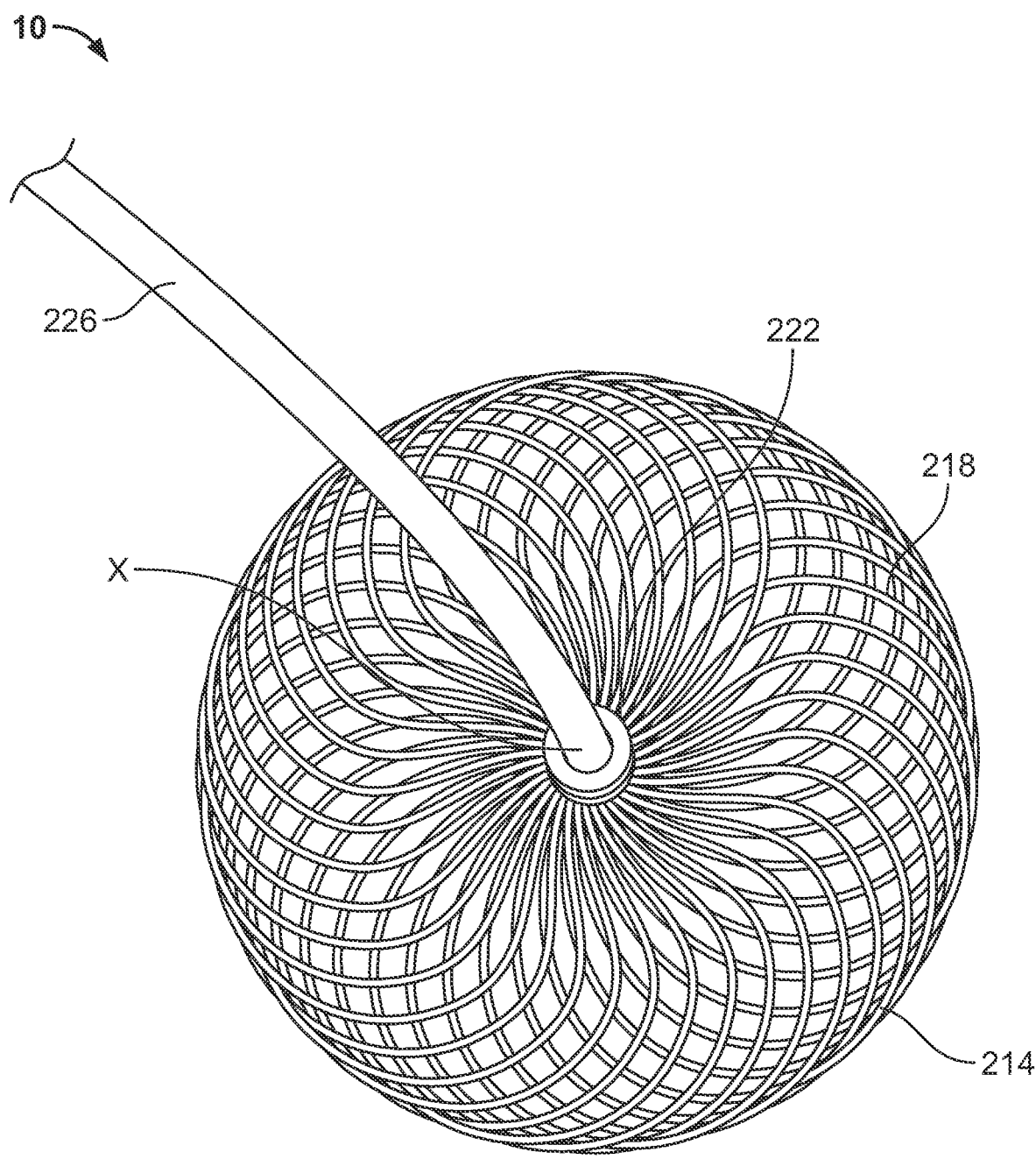
FIG. 11B is an axial view of the anchor of FIG. 11A.

An exemplary anchor 210 for a prosthetic mitral heart valve is illustrated in FIGS. 11A and 11B. Anchor 210 includes a first disc 214 and a second disc 218, both provided by a wire mesh and centered on an axis X. First disc 214 is offset from second disc 218 in a first direction along axis X. First disc 214 and second disc 218 are each biased toward a dome-shaped resting configuration that is concave toward a second direction along axis X, the second direction being opposite the first direction. The resting configuration of first disc 214 extends far enough in the second direction along axis X to partially overlap second disc 218.

Figure 12:
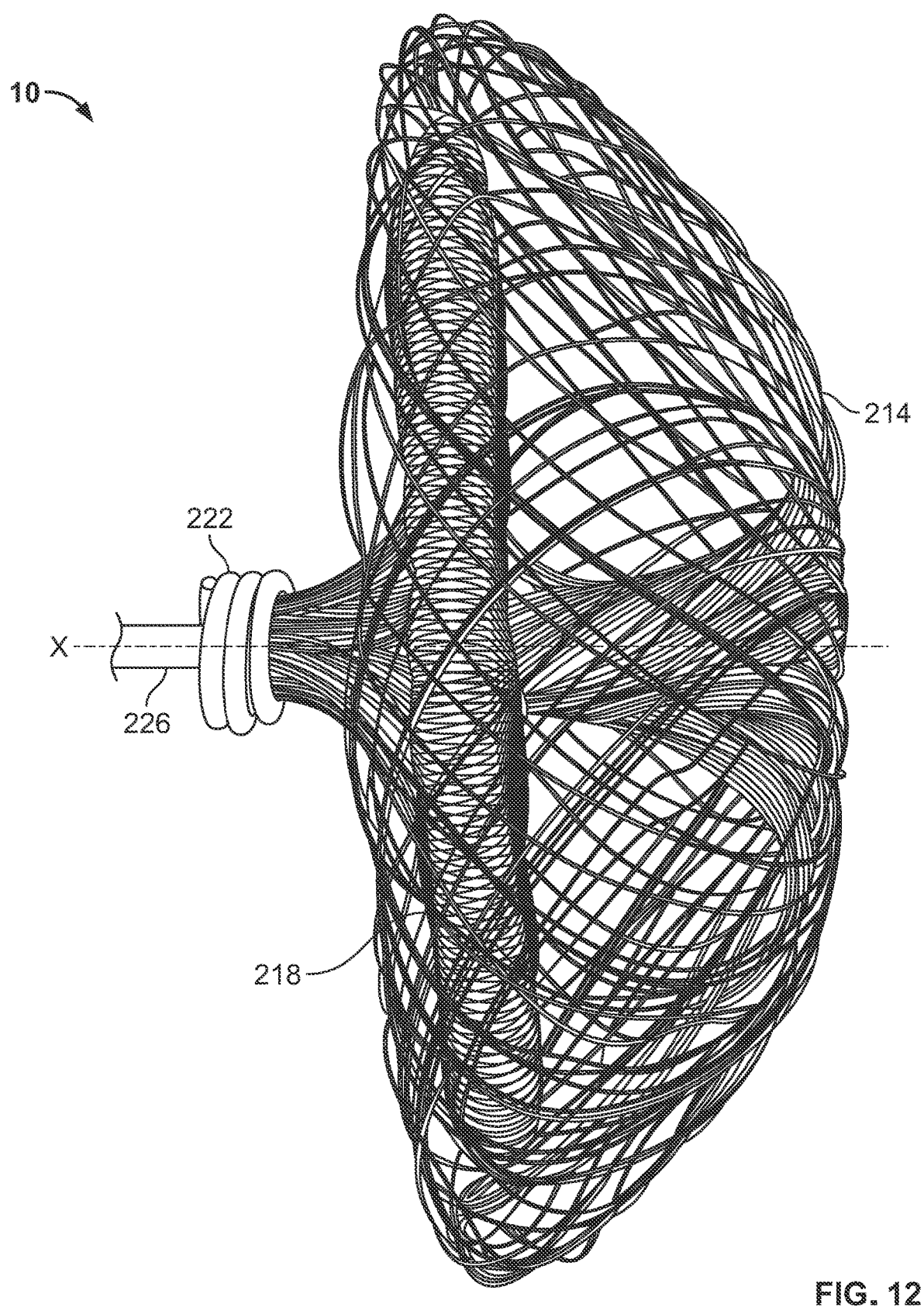
FIG. 12 is a side view of the anchor for the prosthetic valve of FIG. 1 according to another arrangement.

It should be understood that the illustrated dome shapes are merely exemplary, and first disc 214 and second disc 218 may be biased differently. For example, either or both of first disc 214 and second disc 218 may be biased toward a resting configuration that is convex toward the second direction or generally planar. Further, the first disc 214 and second disc 218 may be biased to different resting configurations. In one example, the first disc 214 may be biased toward a dome-shaped resting configuration that is concave toward the second direction while the second disc 218 is biased toward a generally planar configuration having about the same diameter location as the widest part of the dome-shaped resting configuration of the first disk 214, as shown in FIG. 12. In the arrangement shown in FIG. 12, second disc 218 is generally planar in shape with a shallow concavity toward the first direction near the center of second disc 218.

Anchor 210 may also include a cuff 222 for gripping a tether 226, which may be connected to a prosthetic heart valve. Cuff 222 is offset from second disc 218 in the second direction along axis X. One-way gripping features, such as angled teeth, within cuff 222 may permit anchor 210 to slide along tether 226 in the second direction, but not the first direction. In other embodiments, cuff 222 may be fixedly attached to tether 226 so that the anchor 210 may not slide along the tether.

Figure 13:
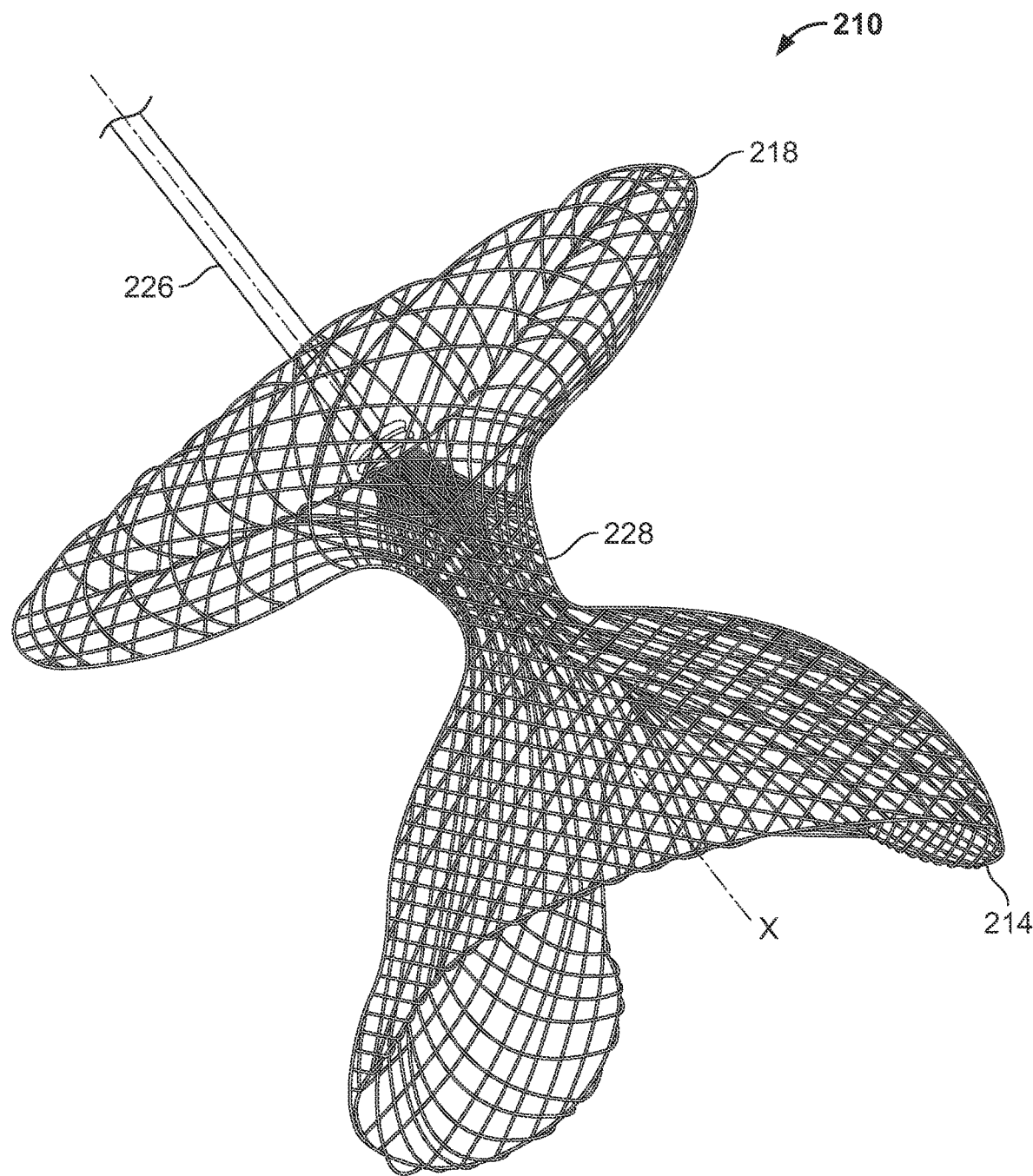
FIG. 13 is a perspective view of the anchor of FIG. 11 in a partially everted state.

Anchor 210 is flexible, as illustrated in FIG. 13, which shows anchor 210 with the first disc 214 everted from its resting configuration. First disc 214 is connected to second disc 218 by a neck 228 extending between first disc 214 and second disc 218. In the illustrated example, neck 228 is centered on axis X, but in other examples neck 228 may be radially offset from axis X. First disc 214, second disc 218, and neck 228 may all be constructed from a single continuous piece or tube of wire mesh. The wire mesh may be formed from a plurality of strands or wires braided into various three-dimensional shapes and/or geometries to engage tissues, or from one or more sheets cut to provide mesh, such as by laser. In one example, the wires form a braided metal fabric that is resilient, collapsible and capable of heat treatment to substantially set a desired shape. One class of materials which meets these qualifications is shape-memory alloys, such as nitinol. The wires may comprise various materials other than nitinol that have elastic and/or memory properties, such as spring stainless steel, trade-named alloys such as Elgiloy® and Hastelloy®, CoCrNi alloys (e.g., tradename Phynox), MP35N®, CoCrMo alloys, or a mixture of metal and polymer fibers. Depending on the individual material selected, the strand diameter, number of strands, and pitch may be altered to achieve the desired shape and properties of anchor 210. Shape memory materials such as nitinol may be particularly suitable for anchor 210 in that shape memory material construction enables anchor 210 to consistently return to an intended shape after being compressed and deployed. In other arrangements, anchor 210 may be covered by or may incorporate other flexible biocompatible material, such as a fabric.

Figure 14:
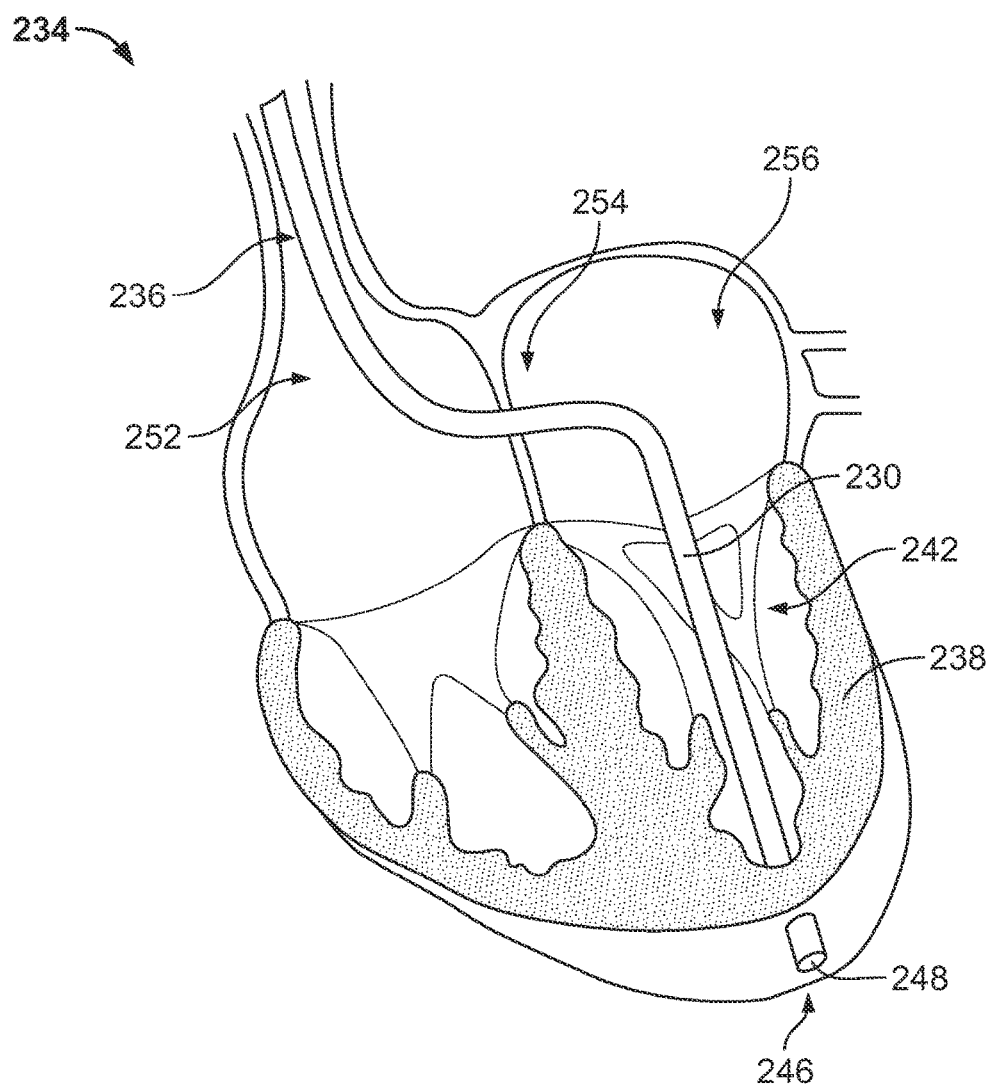
FIG. 14 illustrates a trans-jugular insertion of a delivery tube for the anchor of FIG. 11.

FIG. 14 shows a trans-jugular insertion of an at least partially flexible delivery tube 230 for anchor 210 and valve 110. Delivery tube 230 may be formed of any known material for building catheters, including biocompatible metals such as steel, and may be part of a steerable or flexible catheter system. Delivery tube 230 may include an inflexible portion near its distal end to facilitate the intended puncture of tissue and guidance of valve 110. Delivery tube 230 is inserted through the patient's jugular vein (not shown), then through superior vena cava 236, right atrium 252, atrial septum 254, left atrium 256, native mitral valve 260, and into left ventricle 242. Tube 230 exits left ventricle 242 through ventricular wall 238 at or near the apex 246 of heart 234. A retractable puncturing device (not shown) and a retractable atraumatic tip (not shown) may extend from the distal open end 248 of tube 230 in alternate stages of insertion of tube 230. The puncturing device may produce openings through atrial septum 254 and ventricular wall 238 while the atraumatic tip may act to prevent injury to other tissue. Once delivery tube 230 has been fully inserted, the distal open end 248 of tube 230 is positioned outside of ventricular wall 238. The trans-jugular insertion of tube 230 may be accomplished by any of variety of methods, such as, for example, guiding tube 230 along a guide wire, such as a shape-memory guide wire, inserted through the jugular vein. The flexible nature of anchor 210 allows trans-jugular delivery of anchor 210 through tube 230. Because tube 230, anchor 210, and valve 110 all reach heart 234 from the jugular vein, valve 110 and anchor 210 may be delivered and implanted without any intercostal puncture.

Figure 15:
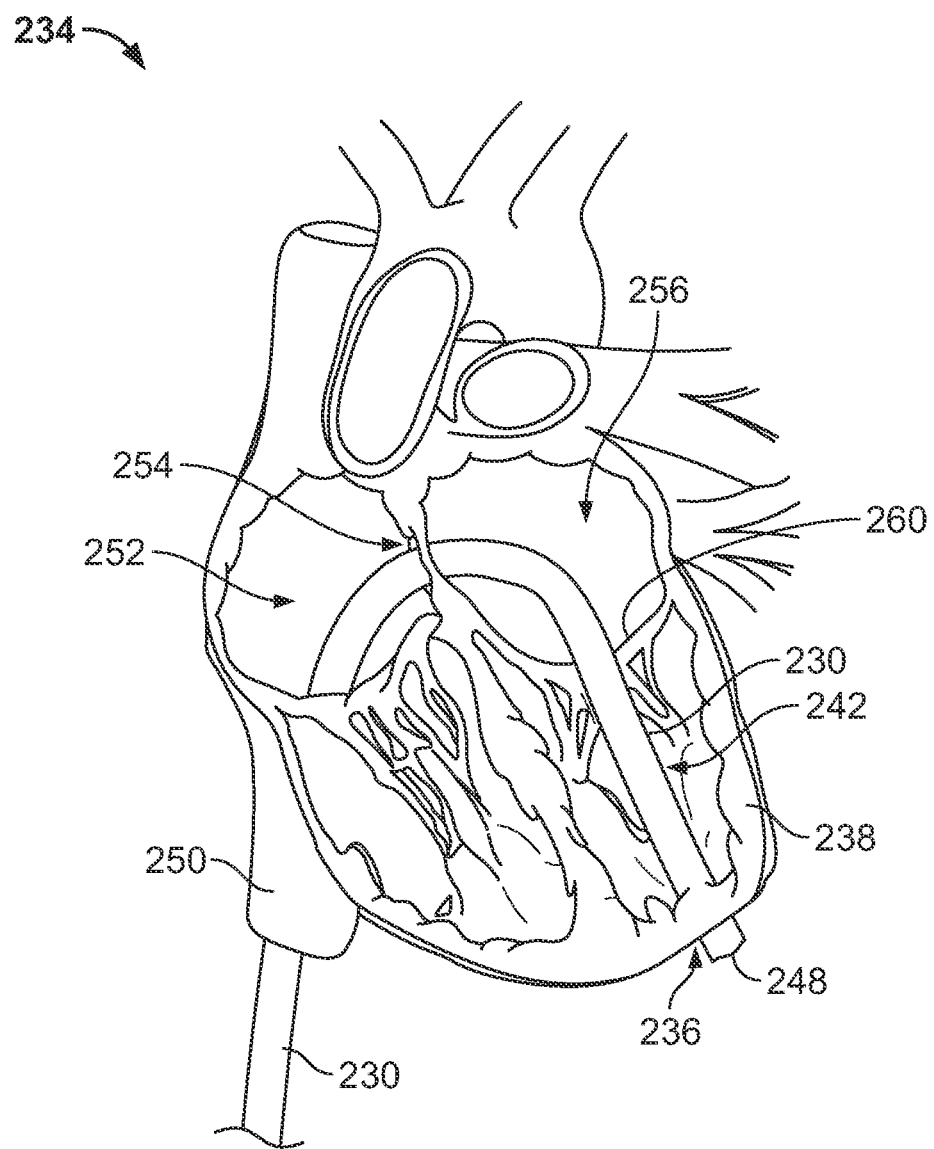
FIG. 15 illustrates a trans-femoral insertion of the delivery tube of FIG. 14.
Figure 16:
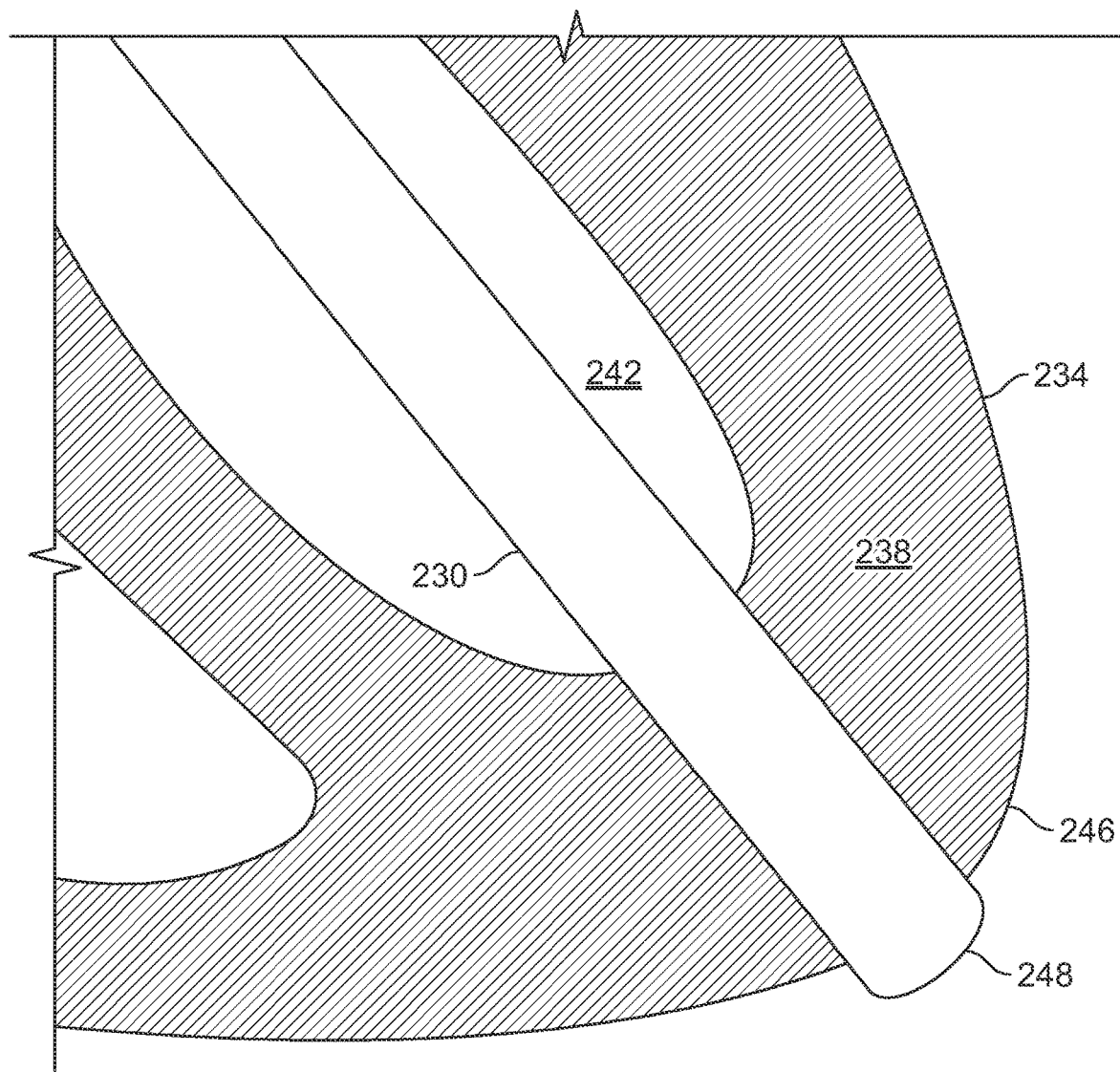
FIG. 16 illustrates the delivery tube of FIGS. 14 and 15 extending through a wall of a heart.

FIG. 15 shows a trans-femoral insertion of tube 230. Tube 230 enters heart 234 through inferior vena cava 250, travels through right atrium 252, and punctures septum 254 to enter left atrium 256. Tube 230 is advanced from left atrium 256 through native mitral valve 260, left ventricle 242, and ventricular wall 238 such that the open end 248 of the tube is positioned outside of wall 238 at or near apex 246. As with trans-jugular insertion, guidance of tube 230 during trans-femoral insertion may be accomplished using a variety of methods, including guidance along a guide wire.

The trans-jugular and trans-femoral insertions described above are merely exemplary. It should be understood that tube 230 could be guided toward heart 234 using any suitable method known in the art.

Figure 17:
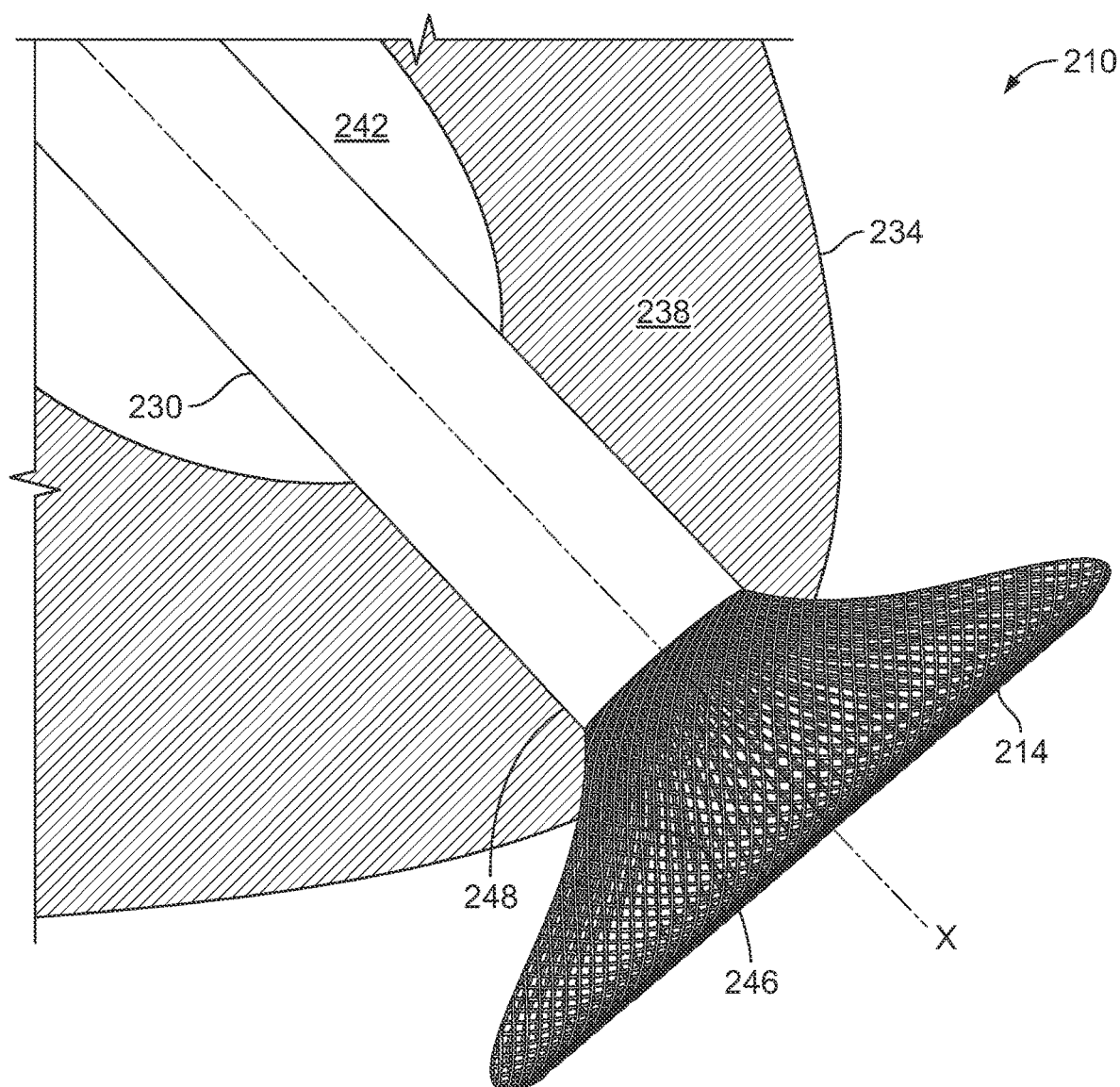
FIGS. 17-20 illustrate the anchor of FIG. 11 in progressive stages of deployment from the delivery tube of FIGS. 14 and 15.
Figure 18:
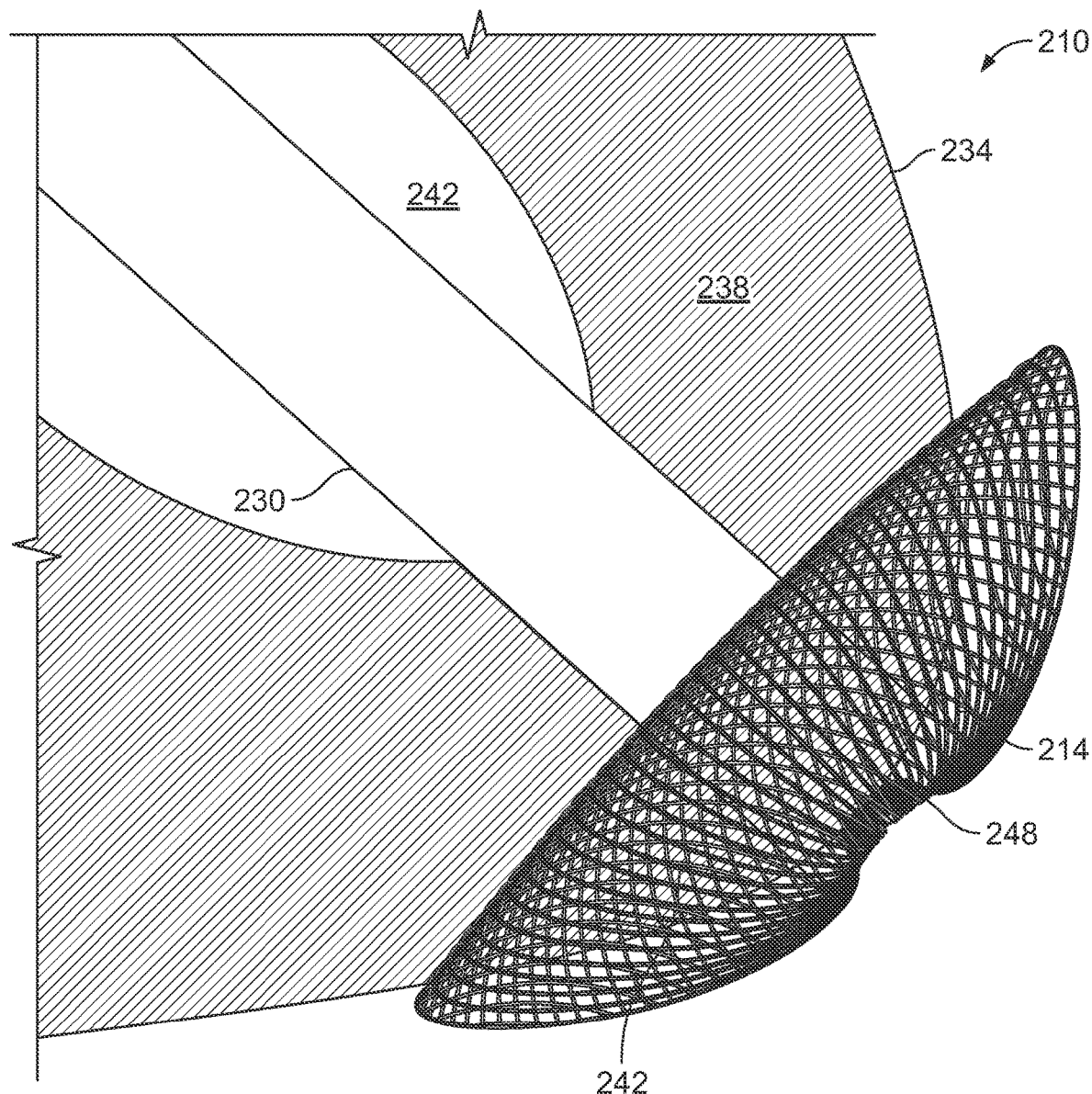
Figure 19:
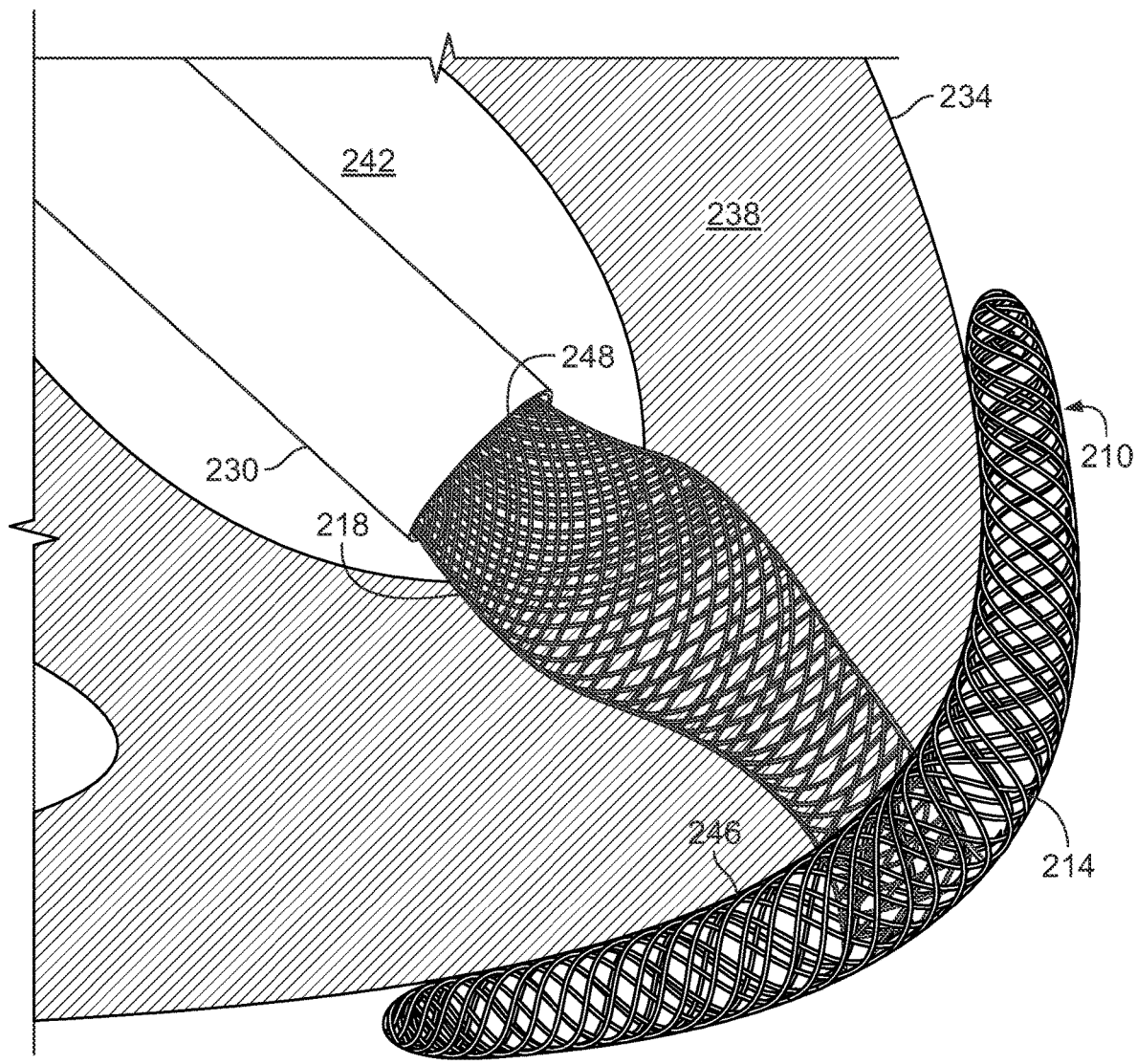
Figure 20:
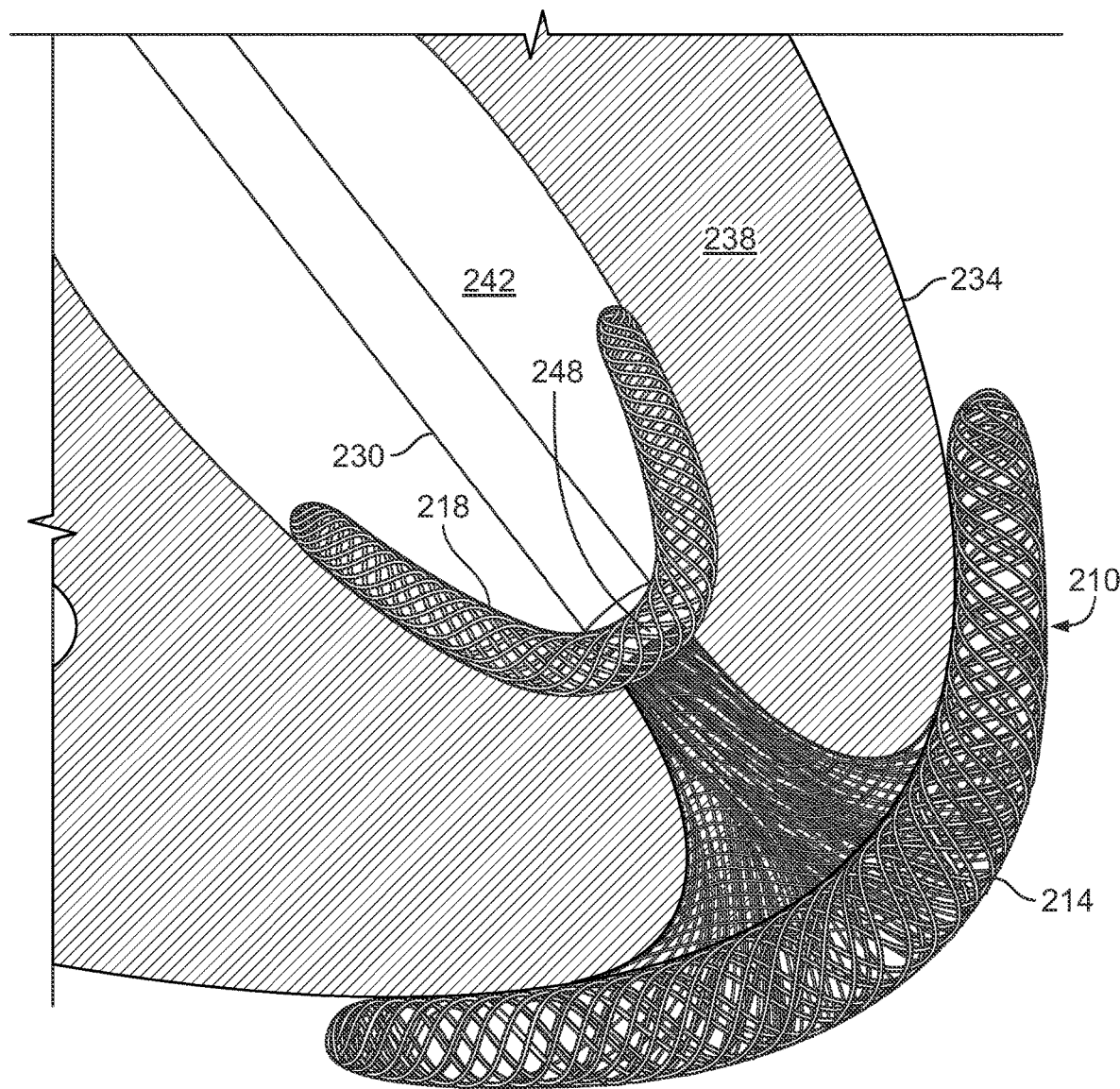
Figure 21A:
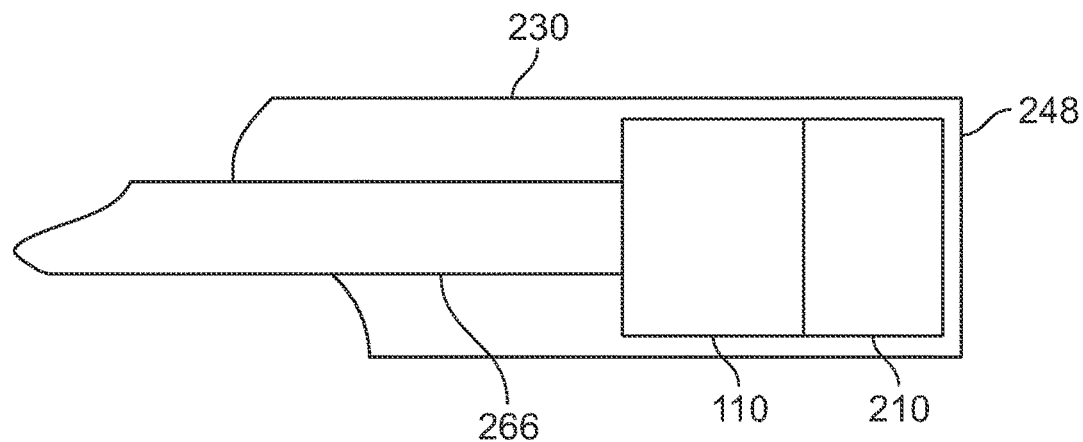
FIGS. 21A and 21B illustrate the delivery tube being retracted from the prosthetic valve of FIG. 1 and the anchor of FIG. 11.
Figure 21B:
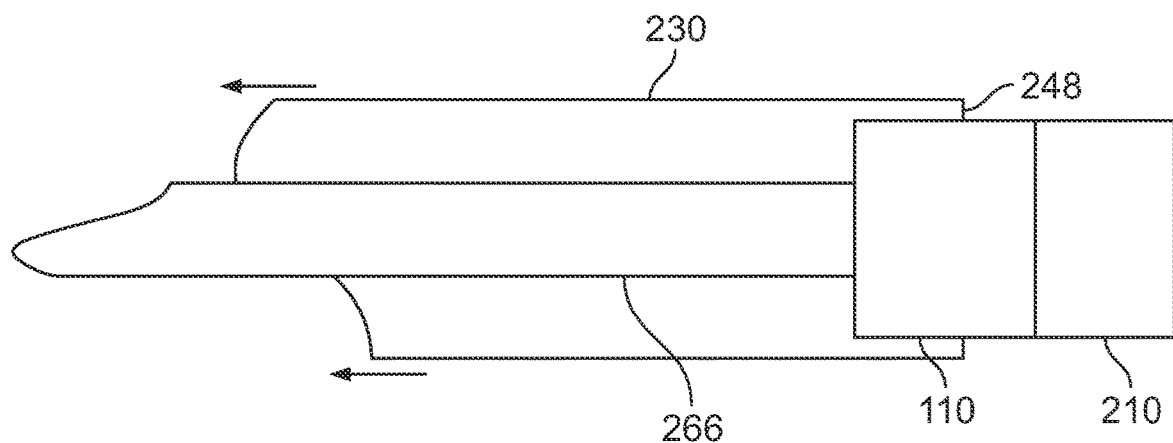

FIGS. 16-20 illustrate anchor 210 in progressive stages of deployment from the open end 248 of tube 230. Tube 230 is shown in a distalmost position in FIG. 16, with open end 248 positioned outside of heart 238. Tube 230 may be retracted while anchor 210 is forced to remain in place, such as by a reversal of a typical Bowden cable arrangement. For example, a semi-rigid cable or wire 266 may be inserted through tube 230, so that a distal end of the semi-rigid cable or wire 266 is in contacting abutment with the proximal end of valve 110, as shown in FIG. 21A. In other words, the distal end of the semi-rigid cable or wire 266 does not need to be coupled to the valve 110, and the semi-rigid cable or wire 266 may function similarly as a push rod by providing a force that prevents the valve 110 from being withdrawn with the tube 230 as the tube 230 is pulled proximally. Thus, pulling tube 230 proximally relative to semi-rigid wire 266 causes valve 110 and anchor 210 to deploy out from the open end 248 of tube 230, as shown in 21B. Semi-rigid cable or wire 266 may have a hollow interior to allow other components, such as tether 226, to extend therethrough. As shown in FIG. 17, retracting tube 230 while preventing anchor 210 from retreating with the tube into heart 234 causes first disc 214 of anchor 210 to deploy out from the open end 248 of tube 230 and expand radially relative to axis X. Upon further retraction of tube 230, the bias of first disc 214 causes it to curve back onto the outer apex 246 of heart 234, as shown in FIG. 18. Further retraction of tube 230 in FIG. 19 allows second disc 218 to deploy and expand radially relative to axis X within left ventricle 242 until second disc 218 opens to press against an inner side of wall 238, as shown in FIG. 20. Pressure against wall 238 results from the elastic bias of first disc 214 and second disc 218 toward certain resting positions as described above with regard to FIGS. 11A, 11B, and 12. First disc 214 and second disc 218 pressing on opposite sides of wall 238 causes anchor 210 to grip wall 238. Such progressive expansion from within a narrow tube results in anchor 210 adequately securing valve 110 to ventricular wall 238 without requiring an intercostal puncture through the patient's chest.

Figure 22:
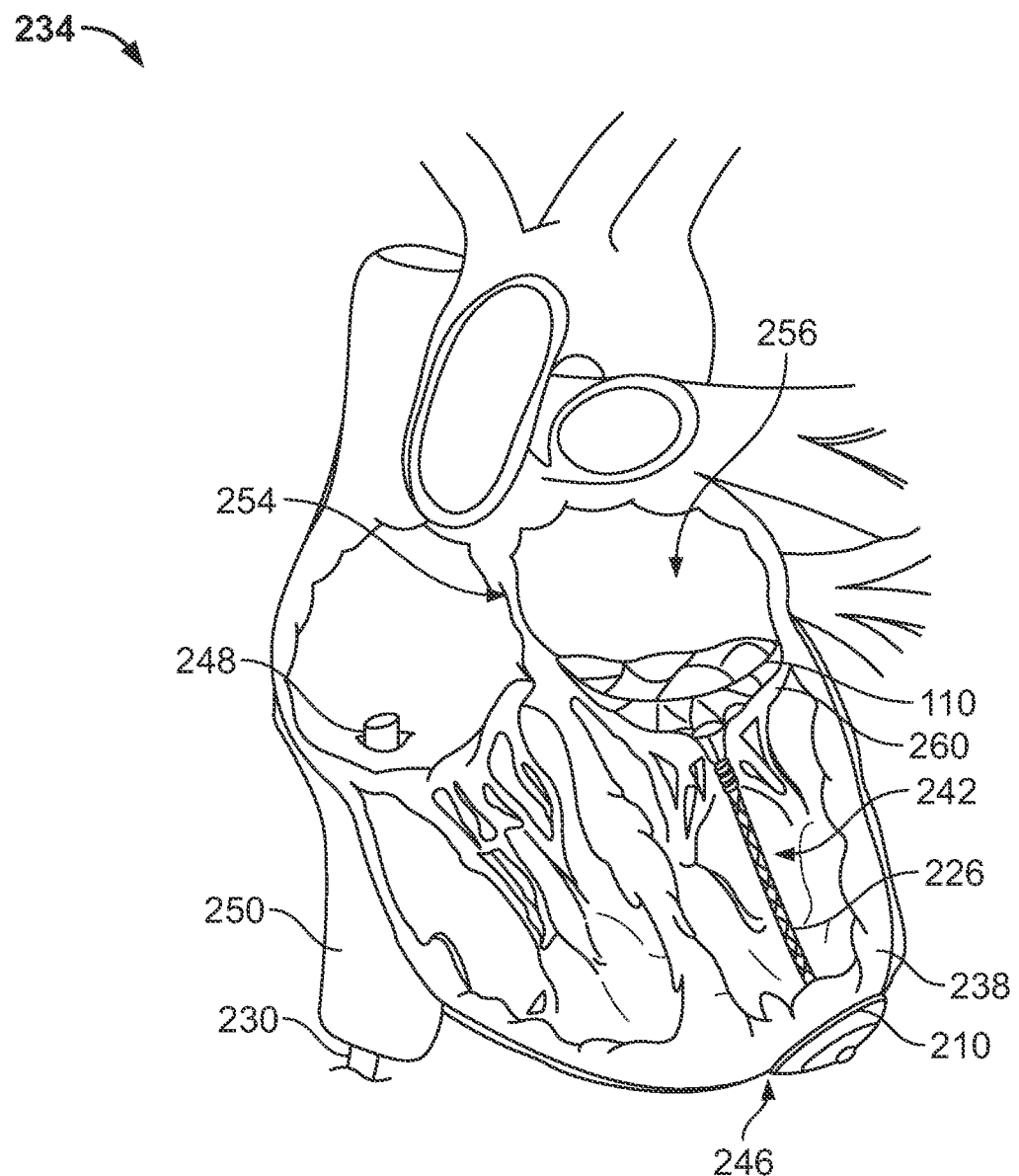
FIG. 22 illustrates the valve of FIG. 1 implanted in a heart.

FIG. 22 illustrates valve 110 implanted in heart 234 with anchor 210 seated at or near the apex 246 of heart 234. Tube 230 has been withdrawn from heart 234, through inferior vena cava 250 in the illustrated example, leaving valve 110 behind.

Figure 23:
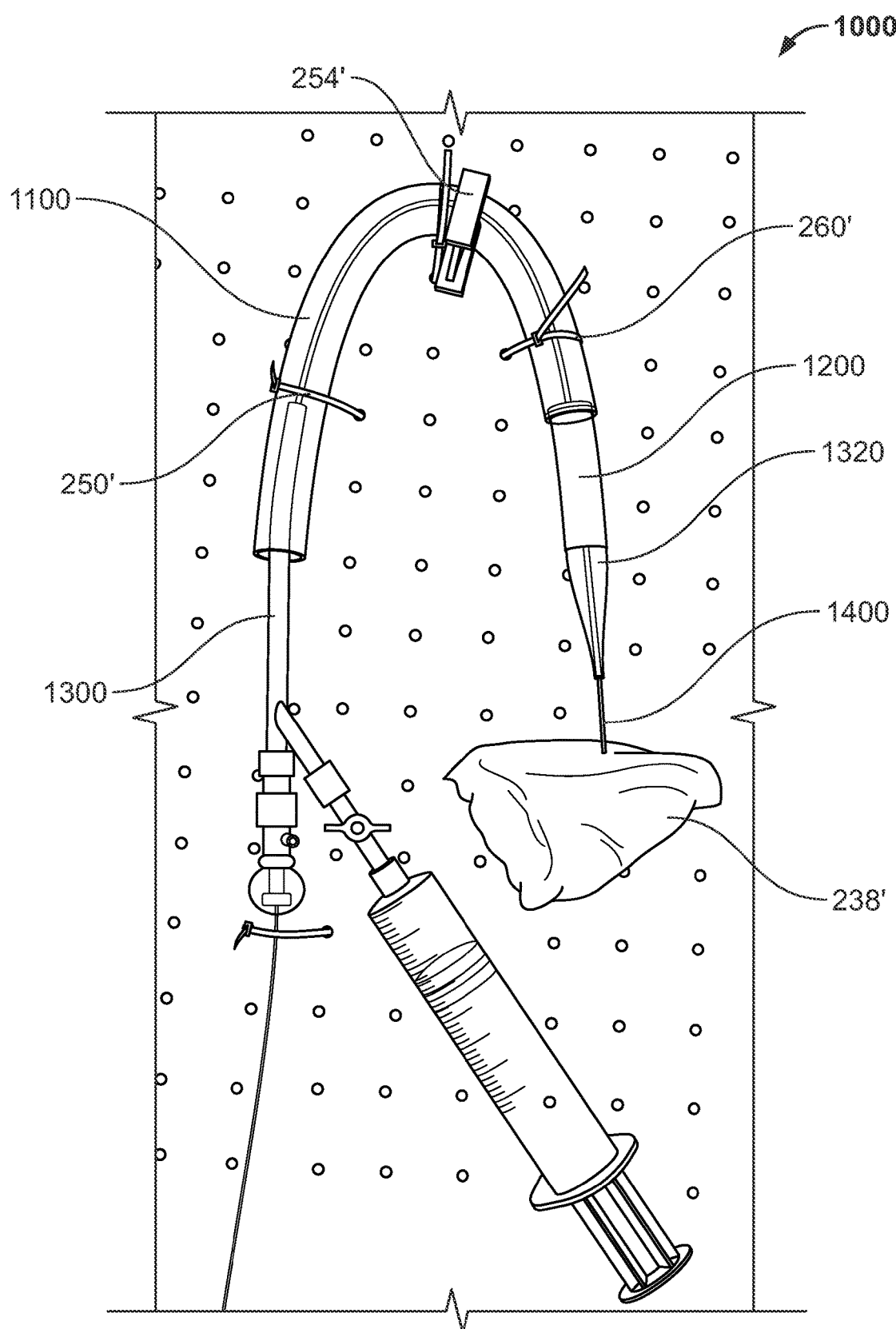
FIGS. 23-27 illustrate steps in a method of creating a transapical puncture from inside the heart.

Other apparatus and methods may also be suitable for delivering a tether anchor to the ventricular apex without requiring an incision in the patient's chest. FIG. 23 illustrates a delivery catheter 1000 suitable for delivery and deployment of an expandable tether anchor to the ventricular apex. Generally, catheter 1000 is illustrated in FIGS. 23-27 attached to a board, with ties representing anatomical structures, including the exit of the inferior vena cava 250', the atrial septum 254', and the native mitral valve 260'. The ventricular wall 238' is represented by chicken breast. It should be understood that the model provided in FIGS. 23-27 may be delivered via the inferior vena cava or the superior vena cava, similar to the delivery routes described in connection with FIGS. 14 and 15.

Generally, delivery catheter 1000 may include a port catheter 1100, which may be the outermost portion of delivery catheter 1000. Port catheter 1100 may be used to "port" through the tortuous anatomy. Delivery catheter 1000 may also include an epicardial pad or anchor catheter 1200, which may be positioned radially inward of port catheter 1100, and may function to hold and help deliver an anchor, including but not limited to the expandable tether anchor 210 described above. However, in some embodiments, the anchor catheter 1200 may be the outermost catheter and may also have a function similar to port catheter 1100, with the port catheter being omitted from delivery catheter 1000. Delivery catheter 1000 may further include a balloon catheter 1300, which may be positioned radially inward of anchor catheter 1200. Balloon catheter 1300 may end in an expandable member or balloon 1320 at or near a distal end of the balloon catheter. The balloon catheter 1300 may be in fluid communication with balloon 1320 so that fluid, such as saline, may be passed through the balloon catheter 1300 to inflate balloon 1320. Still further, delivery catheter 1000 may include a guide wire and/or needle 1400, which may be positioned radially inward of the balloon catheter 1300 and balloon 1320. The needle 1400 may include a sharp distal tip and may function to pierce through tissue. The needle 1400 may be solid or, in other embodiments, it may have a hollow interior. In one embodiment, the needle 1400 may be a sharpened guidewire having an outer diameter of about 0.035 inches. In another example, the needle 1400 may be a BRK™ Transseptal Needle, offered by Abbott Labs. It should be understood that, as used herein, the term "sharp distal tip" refers to a leading end of an object that has an edge and/or point adapted for cutting and/or piercing tissue.

In use, the delivery catheter 1000 may be advanced into the right atrium of a patient, for example via a transjugular delivery route through the superior vena cava, or a transfemoral delivery route through the inferior vena cava. Regardless of the delivery route, the distal tip of needle 1400 is preferably positioned proximal of the distal tip of balloon 1320 during delivery so as to reduce the risk of unintentionally piercing any tissue during this delivery step. If port catheter 1100 is included in delivery catheter 1000, the distal end of anchor catheter 1200 may be positioned proximal to, or aligned with, the distal end of the port catheter during this delivery step. The balloon 1320 may be partially or completely inflated during delivery, with the balloon extending beyond the distal end of port catheter 1100 (if included) and the distal end of anchor catheter 1200, with the inflated balloon providing an atraumatic leading surface or tip of the delivery catheter 1000 during delivery. In order to provide a suitable atraumatic leading surface, the balloon 1320 may have a tapered shape when inflated.

A proximal end of port catheter 1100 may be coupled directly or indirectly to a handle that remains outside of the patient during the procedure, and the port catheter may include steering elements such as steering wires coupled to that handle to allow the user to steer the port catheter through the vasculature. If port catheter 1100 is omitted, the steering functionality may be provided on the anchor catheter 1200, although in some embodiments both the port catheter and the anchor catheter may include components to allow for steering. With the distal tip of the delivery catheter 1000 being positioned in the right atrium (with or without use of steering of port catheter 1100), the distal tip may be positioned adjacent to the atrial septum 254'. Steering may be used to help position the distal tip of the delivery catheter 1000 at the desired location on atrial septum 254' for a transseptal puncture. With the distal tip of delivery catheter 1000 in the desired position adjacent the atrial septum 254', needle 1400 may be advanced distally beyond balloon 1320, with the needle piercing through the atrial septum 254'. The needle 1400 may be directly or indirectly coupled to the handle of the delivery system to allow for easy manipulation of the needle.

While needle 1400 is being advanced through atrial septum 254', it is preferable that balloon 1320 remains inflated, as the inflated balloon may provide additional stability (e.g. column strength) to the needle and help the needle resist deflecting or bending, although this is not required and the needle may be advanced while the balloon is partially or fully deflated. If needle 1400 punctures atrial septum 254' while balloon 1320 is deflated, the deflated balloon and needle may be advanced simultaneously during the puncturing, in order to position the deflated balloon within the transseptal puncture.

After needle 1400 has punctured the atrial septum 254', balloon 1320 is preferably deflated, for example by with-drawing fluid from the balloon via balloon catheter 1300. With balloon 1320 deflated, balloon catheter 1300 may be advanced distally (with or without corresponding motion of needle 1400) in order to position a portion of the deflated balloon within the punctured atrial septum 254'. If desired, the transseptal puncture may be increased in size to provide sufficient space for the passage of other portions of delivery catheter 1000, such as port catheter 1100 (if used) and anchor catheter 1200. To increase the size of the transseptal puncture, balloon 1320 may be inflated while positioned within the transseptal puncture. If balloon 1320 is tapered, it may be advanced through the transseptal puncture while inflated in order to dilate the transseptal puncture to a size sufficient to receive therethrough other components of delivery catheter 1000. Another option is to perform the dilation in a step-wise manner. For example, balloon 1320 may be inflated while the relatively small distal end of the balloon is positioned within the transseptal puncture. Balloon 1320 may then be deflated, and then further advanced a distance distally through the transseptal puncture, and re-inflated to further expand the transseptal puncture. This step-wise dilation may be performed in any number of desired steps. After the transseptal puncture is sufficiently dilated, port catheter 1100 (if included) and anchor catheter 1200 may be advanced into the left atrium.

It should be understood that, in other embodiments, a separate tool may be used to create the transseptal puncture, and the delivery catheter 1000 may then be advanced through the atrial septum. However, it is generally preferable for delivery catheter 1000 to create the septal puncture in order to reduce the required time for the procedure and the number of components involved.

Figure 24:
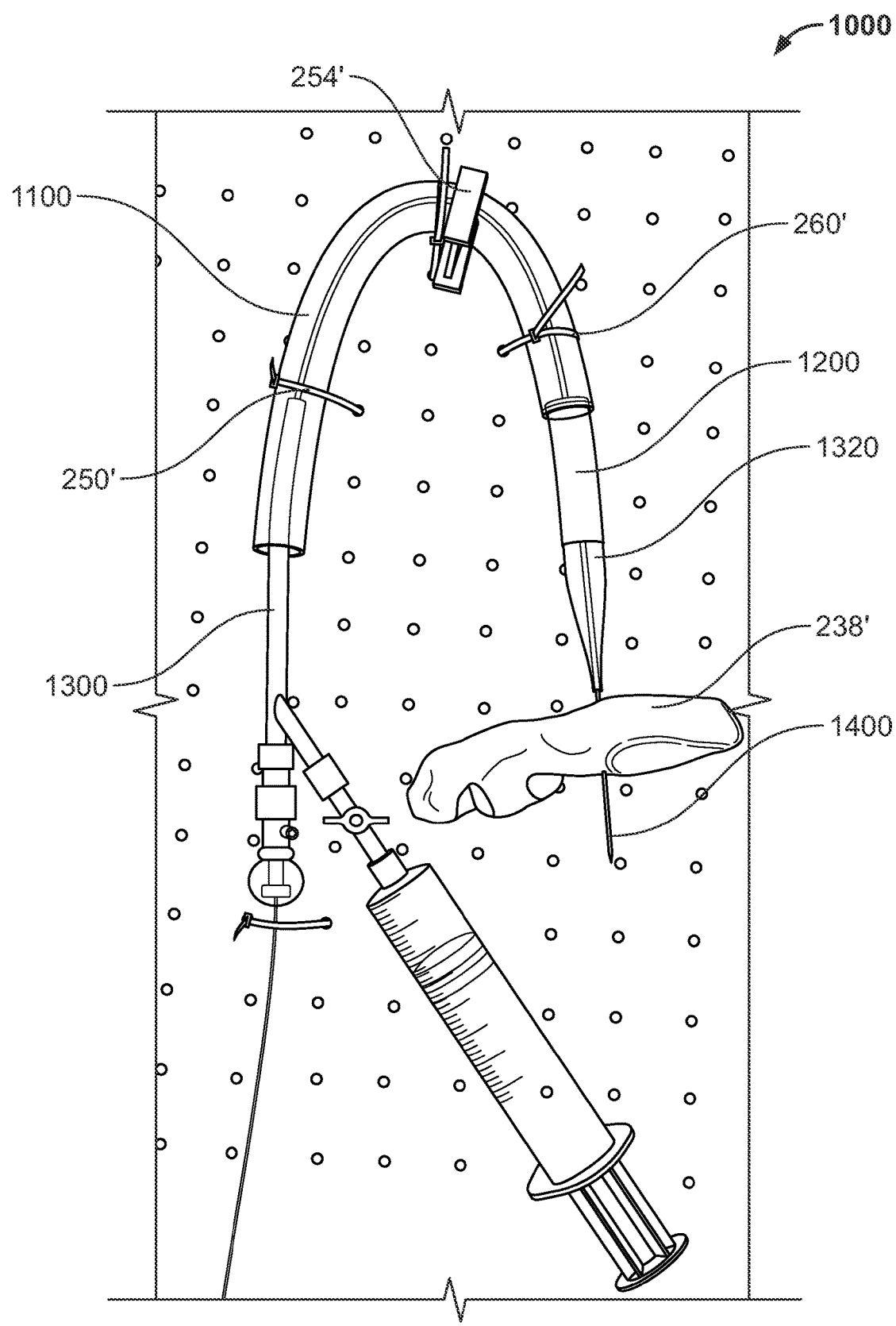

With the port catheter 1100 in the left atrium, the port catheter may be positioned, for example via the steering mechanism, so that the distal tip of the port catheter is substantially perpendicular to the plane of the annulus of the native mitral valve 260'. In other words, the distal end of port catheter 1100 is preferably positioned along an axis that is substantially co-axial with a longitudinal axis passing through the center of the annulus of the native mitral valve 260'. This relative positioning between port catheter 1100 and the native mitral valve 260' may provide an optimum positioning for further steps of the procedure. For example, while the port catheter 1100 is aligned with the central longitudinal axis of the native mitral valve 260', the anchor catheter 1200 may be advanced distally so that the anchor catheter passes through the native mitral valve and into the left ventricle. Further, the position of the port catheter 1100 may, at least in part, determine the position of the anchor delivered via the delivery catheter 1000. Typically, it is desirable that the anchor is positioned substantially perpendicular to the plane of the annulus of the native mitral valve 260', as this orientation may desirably result in the tether attached to the anchor extending towards the longitudinal center of the mitral valve. As the anchor catheter 1200 is passing through the native mitral valve 260', it may be desirable for the balloon 1320' to be partially or fully inflated and extend beyond the distal tip of the anchor catheter, so that an atraumatic tip of the delivery catheter 1000 is provided. This may avoid unintentionally damaging the patient's anatomy, and may also help avoid the distal tip of the delivery catheter 1000 getting caught or otherwise entangled within the native chordae tendineae. Similarly, during the advancement of anchor catheter 1200 into the left ventricle, needle 1400 is preferably retracted within balloon 1320 so that the sharp distal tip of the needle is not exposed. With the tip of the balloon 1320 positioned adjacent or in contact with the ventricular wall 238', as shown in FIG. 23, needle 1400 may again be advanced distally beyond the balloon to pierce the ventricular wall, as shown in FIG. 24.

Figure 25:
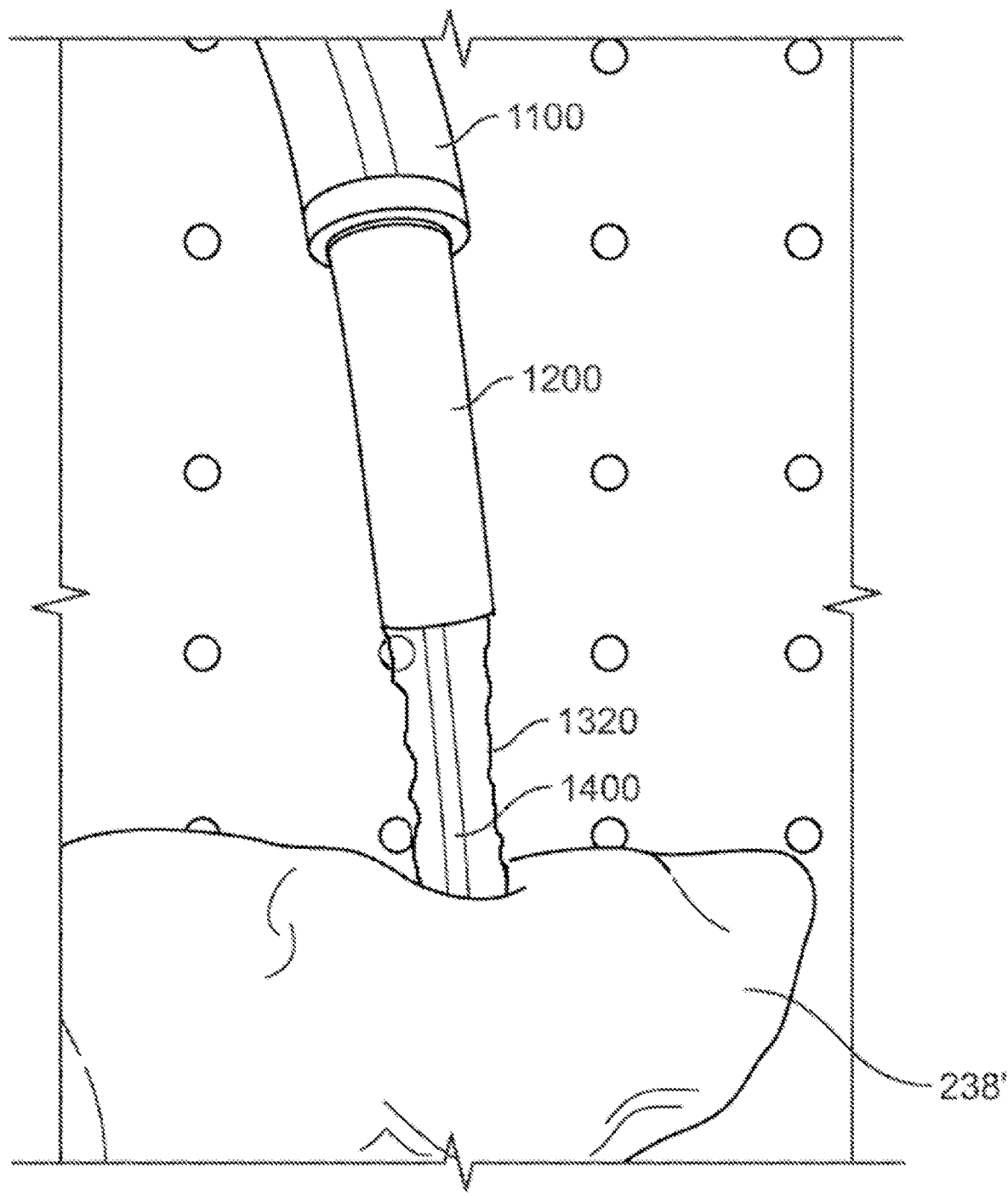

After needle 1400 begins to pierce the ventricular wall 238', or otherwise simultaneously with the needle piercing the ventricular wall, balloon 1320 and balloon catheter 1300 may be advanced distally with the needle, while the balloon is still inflated. Advancement of the balloon 1320 and needle 1400 may continue until heavy resistance is felt by the user. At this point, as shown in FIG. 25, balloon 1320 may be deflated, similar to the process described above for creating the transseptal puncture.

Figure 26:
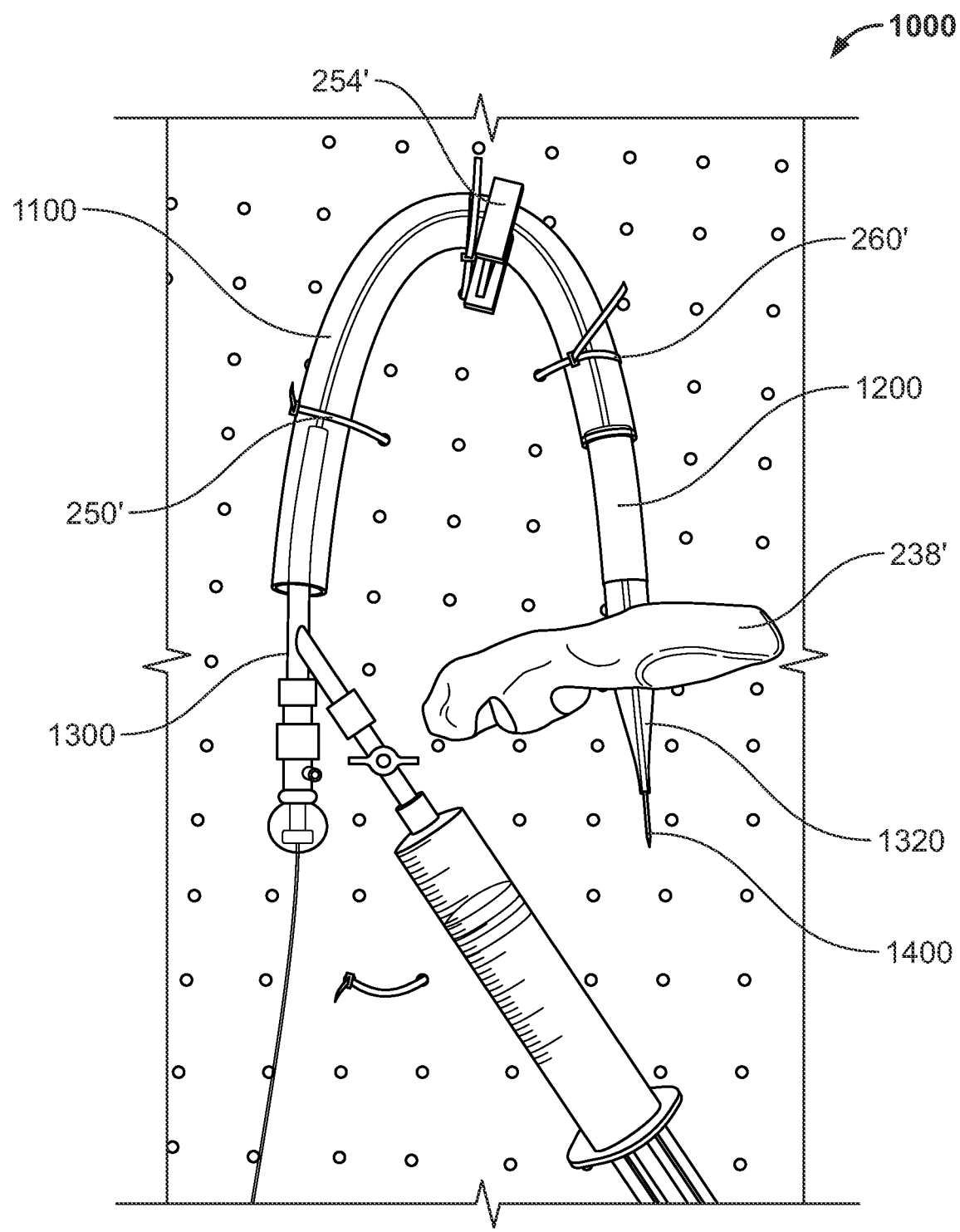
Figure 27:
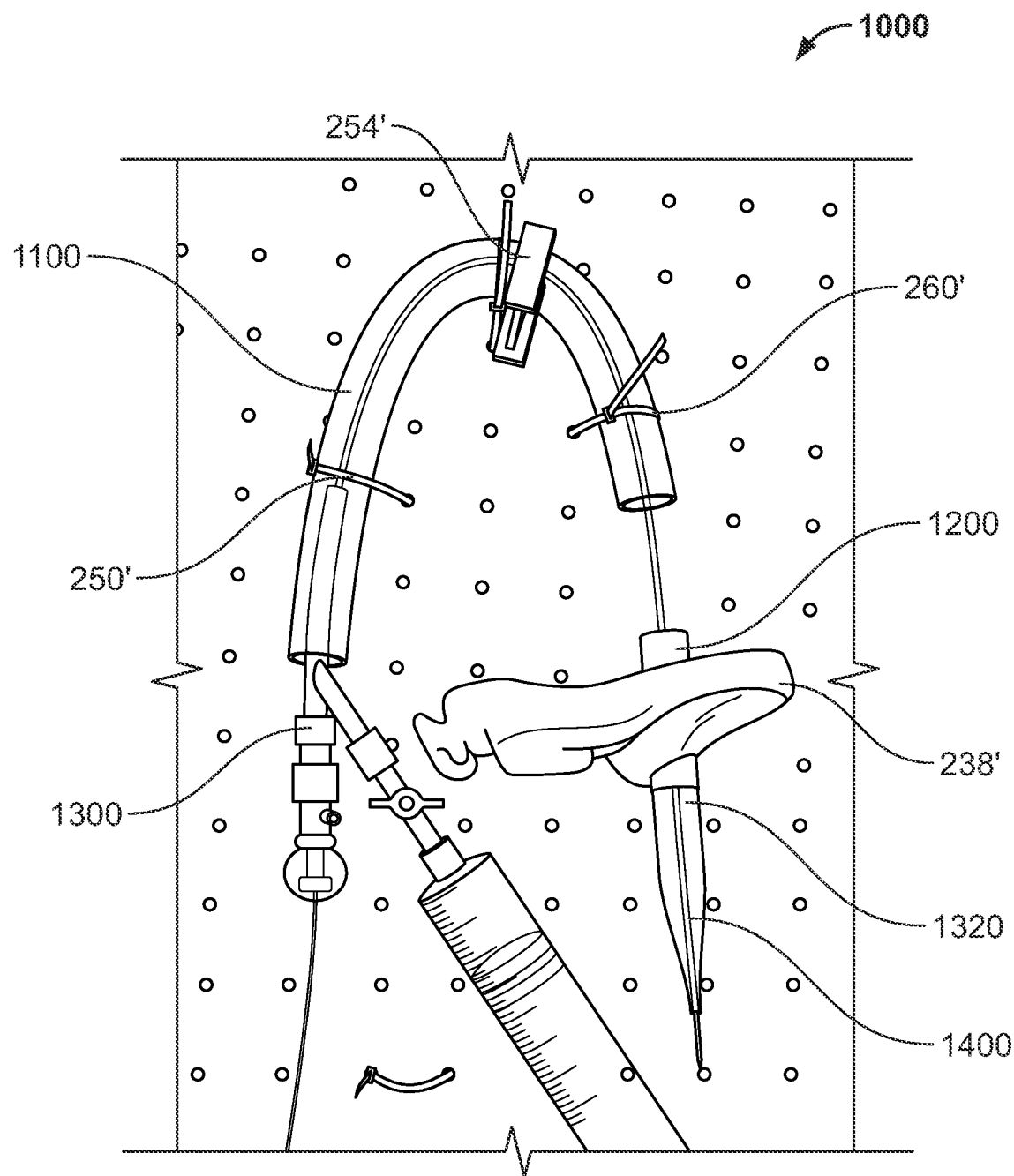

After balloon 1320 is deflated, the balloon may be further advanced into the myocardium of the ventricular wall 238' until a larger diameter portion of the balloon is surrounded by tissue of the ventricular wall. This advancement of balloon 1320 may be simultaneous with advancement of needle 1400. However, in other embodiments, it may be desirable to retract needle 1400 proximally before advancing the deflated balloon 1320 distally, in order to reduce the risk of the sharp tip of the needle passing beyond the ventricular wall 238' enough distance to damage other nearby tissue. Once a larger diameter portion of balloon 1320 is surrounded by tissue of the ventricular wall 238', the balloon may be inflated again to dilate the transapical puncture. As with the similar procedure described above for dilating the transseptal puncture, the transapical puncture of the ventricular wall 238' may be dilated one time, or multiple times in a step-wise manner until the transapical puncture is large enough, in this case to allow for passage of the anchor catheter 1200. The full dilation of the transapical puncture of the ventricular wall 238' is illustrated in FIG. 26, and passage of anchor catheter 1200 through the ventricular wall is illustrated in FIG. 27. Although anchor catheter 1200 is illustrated in FIG. 27 as having a proximal end that is positioned distal to the distal end of the port catheter 1100, in practice, the anchor catheter preferably has a length that extends to, or near, a handle configured to remain outside the patient during the procedure.

Although the step-wise dilation procedure is described above for both the transseptal puncture and the transapical puncture, it may not be needed in either procedure.

After a portion of the anchor catheter 1200 has passed through the ventricular wall 238', balloon 1320 may be deflated and pulled proximally through the anchor catheter, leaving the distal end of the anchor catheter open so that an anchor may be passed through the anchor catheter for positioning at the apex of the left ventricle. In some embodiments, the anchor may be an expandable anchor similar or identical to anchor 210, which may be kept in a collapsed condition within anchor catheter 1200 just proximal to the balloon 1320 during the delivery procedure.

Figure 28A:
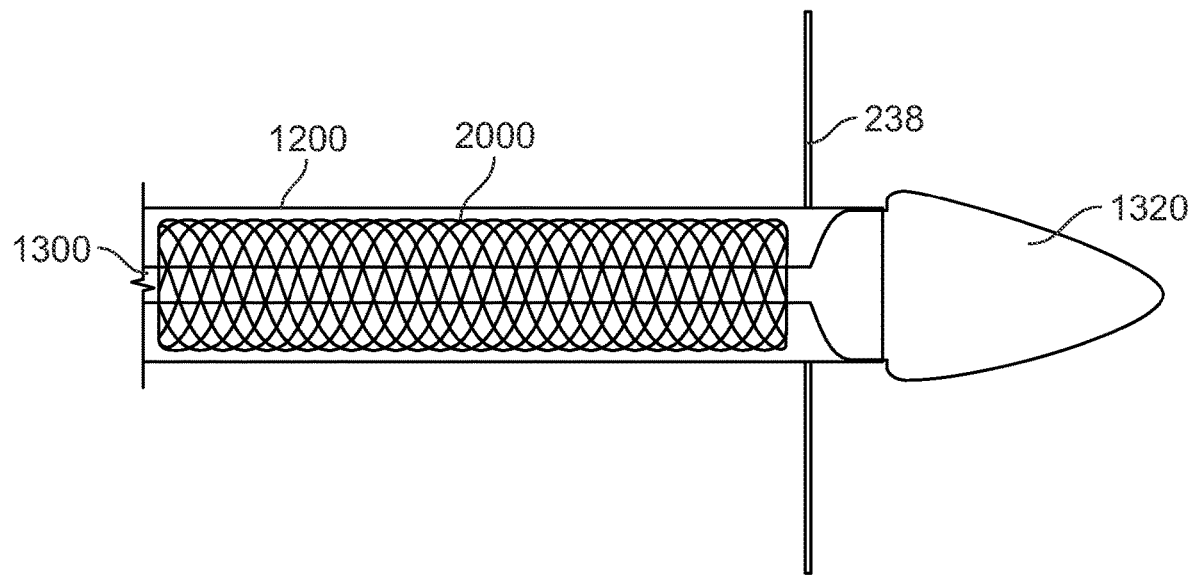
FIGS. 28A-D illustrate steps in a method of deploying an anchor from within the heart using one embodiment of a delivery catheter.
Figure 28B:
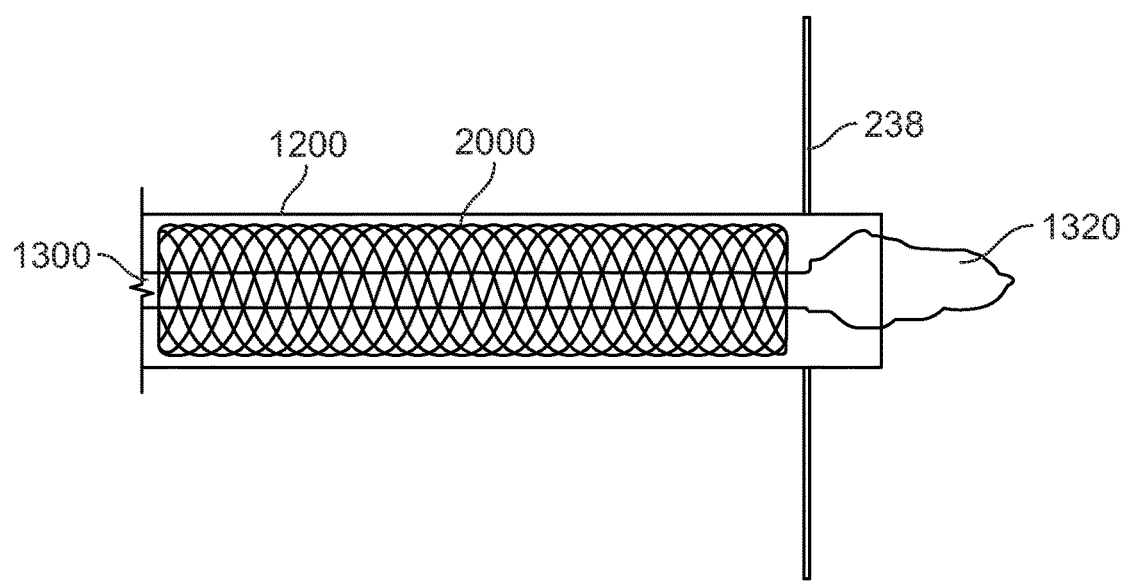
Figure 28C:
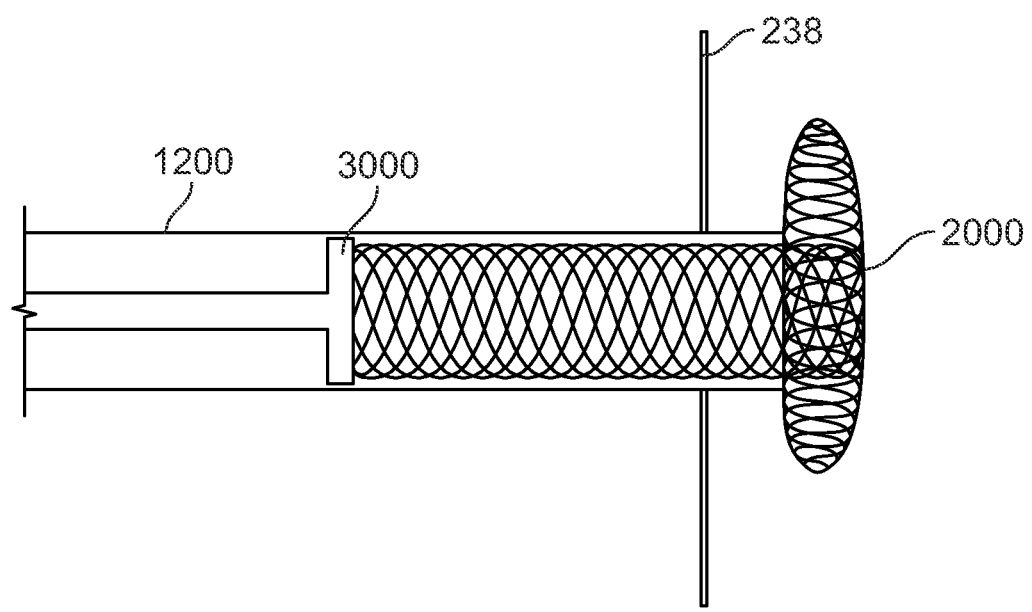
Figure 28D:
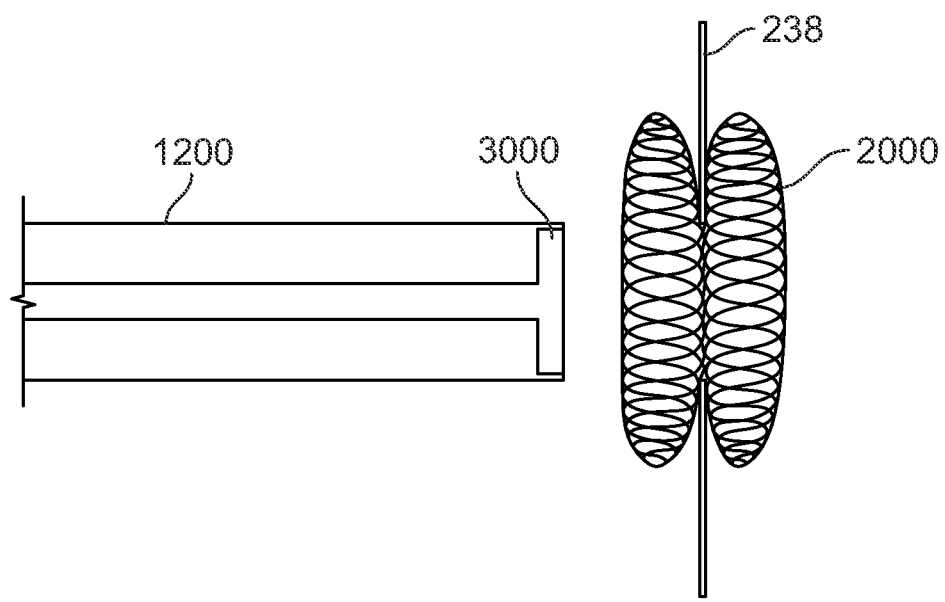

FIGS. 28A-D are highly schematic illustrations of the release of an expandable anchor 2000 that may be generally similar to anchor 210. FIG. 28A illustrates anchor catheter 1200 extending through the ventricular wall 238 with the balloon 1320 of balloon catheter 1300 still inflated, and anchor 2000 in a collapsed condition with the balloon catheter passing through the interior of the anchor. FIG. 28B shows balloon 1320 having been deflated, for example by withdrawal of fluid via balloon catheter 1300. After balloon 1320 is deflated, the balloon and balloon catheter 1300 may be removed proximally through anchor catheter 1200, through the inside of the collapsed anchor 2000. As shown in FIG. 28C, anchor 2000 (or a portion thereof) may be deployed from the distal end of the anchor catheter 1200 on the exterior surface of the ventricular wall 238. This may be accomplished by any suitable method. For example, a push rod 3000 may be positioned proximal the anchor 2000, and the push rod may be pushed distally and/or the anchor catheter 1200 may be pulled proximally to force the anchor out of the open distal end of the anchor catheter. Push rod 3000 may include a shaft with an interior lumen through which balloon catheter 1300 and/or balloon 1320 may be retracted, and within which needle 1400 may be positioned. Needle 1400 is omitted from FIGS. 28A-D for clarity of illustration. The anchor 2000 may be continued to be deployed until it fully exits the anchor catheter 1200, as shown in FIG. 28D. Although not shown in FIG. 28D, a tether similar to tether 226 may be fixed to anchor 2000 and extend proximally through a portion of, or all of, delivery catheter 1000. That tether may be used as a rail over which a prosthetic heart valve, which may be similar to prosthetic heart valve 110, may be delivered. Instead of having the tether fixedly coupled to the prosthetic heart valve, the prosthetic heart valve may include hooks or a similar feature on a portion of the prosthetic heart valve, such as a portion of an inner stent similar to clamping portion 144. The hooks may be directional so that the prosthetic heart valve may be advanced distally over the tether, but not translated proximally. Thus, when the prosthetic heart valve is deployed in the native mitral valve 260, those hooks or similar features may prevent the prosthetic heart valve from migrating toward the left atrium during use. Any excess length of the tether extending proximally to the prosthetic heart valve may be removed from the body, for example by cautery or another suitable method.

Figure 29A:
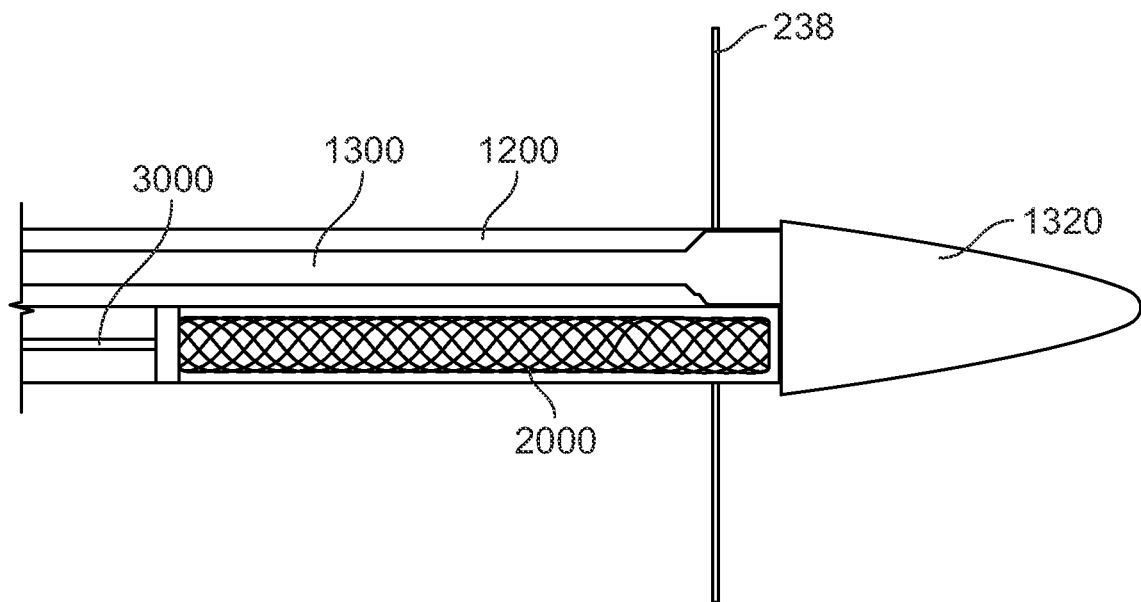
FIGS. 29A-E illustrate steps in a method of deploying an anchor from within the heart using another embodiment of a delivery catheter.
Figure 29B:
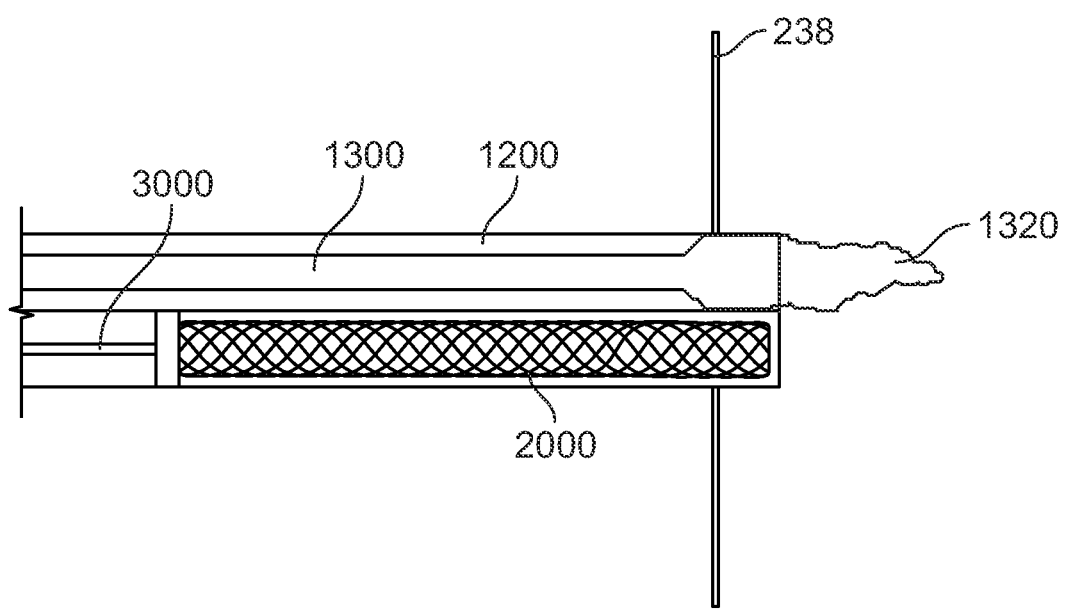
Figure 29C:
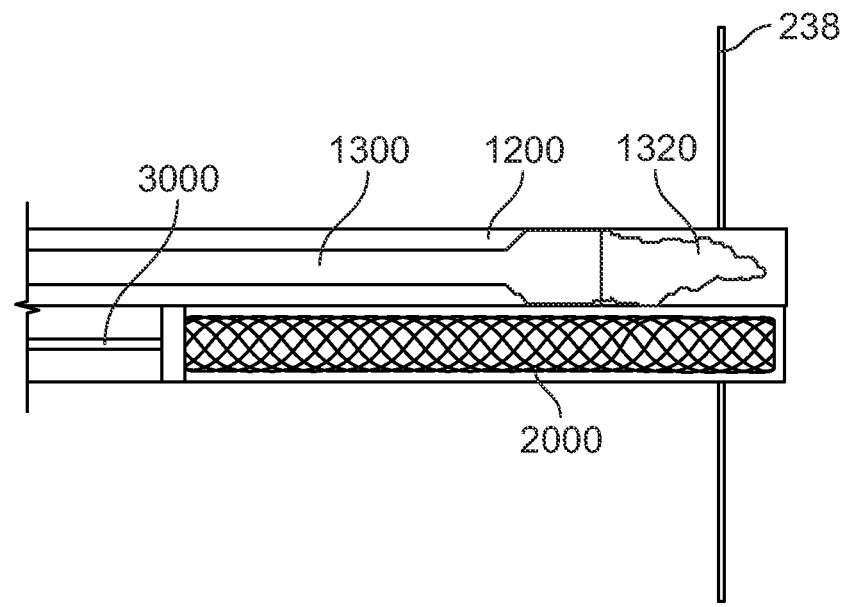
Figure 29D:
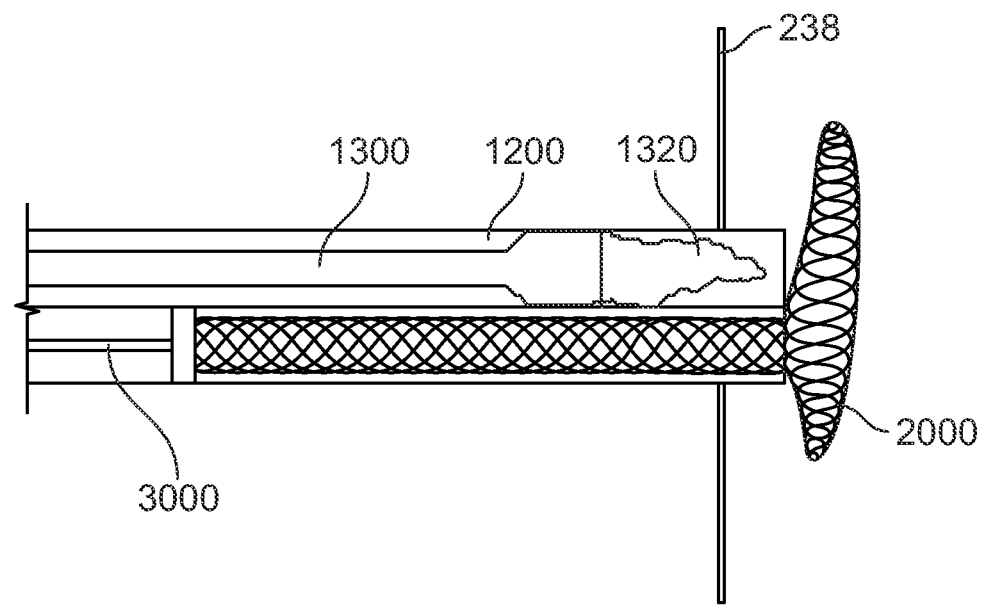
Figure 29E:
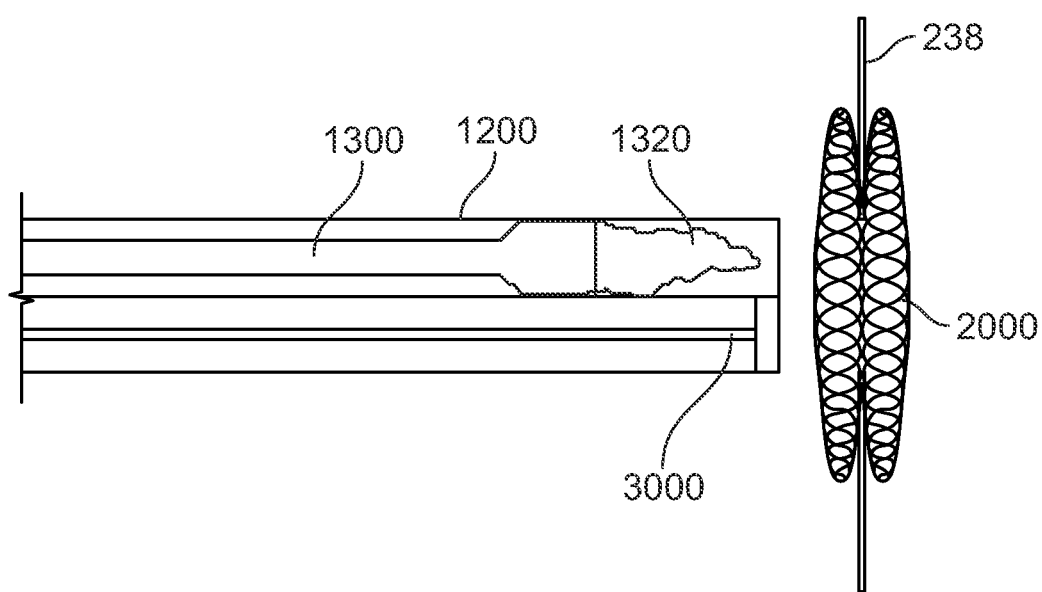

In another embodiment, shown in FIGS. 29A-E, the anchor catheter 1200 may include at least two separate lumens, a first lumen receiving the anchor 2000 and other components, such as push rod 3000, with the balloon catheter 1300 extending through the second lumen. FIG. 29A illustrates anchor catheter 1200 extending through the ventricular wall 238 with the anchor 2000 collapsed in the first lumen, the balloon catheter 1300 extending through the second lumen, and the balloon 1320 still inflated. FIG. 29B shows balloon 1320 having been deflated, after which the balloon and balloon catheter 1300 may be removed proximally through the second lumen of anchor catheter 1200, either partially or fully. FIG. 29C illustrates balloon 1320 and balloon catheter 1300 having been withdrawn into the second lumen of anchor catheter 1200. As shown in FIG. 29D, anchor 2000 (or a portion thereof) may be deployed from the distal end of the anchor catheter 1200 on the exterior surface of the ventricular wall 238. In the illustrated embodiment, push rod 3000 extends through the first lumen of anchor catheter 1200. The push rod 3000 may be pushed distally and/or the anchor catheter 1200 may be pulled proximally to force the anchor out of the open distal end of the anchor catheter. As with FIGS. 28A-D, needle 1400 is omitted from FIGS. 29A-E for clarity of illustration. However, needle 1400 may extend through a lumen in the balloon catheter 1300, such that the tip of the needle may be moved so that the tip of the needle extends beyond distal tip of balloon 1320. The anchor 2000 may be continued to be deployed until it fully exits the anchor catheter 1200, as shown in FIG. 29E. As with the embodiment shown in FIGS. 28A-D, a tether may extend from anchor 2000, and that tether may be coupled to a prosthetic heart valve that is deployed in the native mitral valve 260 to help prevent the prosthetic valve from migrating into the left atrium. For example, one end of the tether may be fixed to the anchor 2000, and the tether may extend proximally through a lumen in push rod 3000.

As should be understood from the above description, the devices and methods described herein may allow for an epicardial anchor or similar device to be positioned on an outer surface of the heart (or within the pericardium) without creating any incisions in the patient's chest. Thus, both a prosthetic heart valve and an anchoring device for that prosthetic heart valve may be delivered in a fully transcatheter manner. This may both reduce complexity of the overall procedure, reduce risks to the patient, and reduce recovery time for the patient.

According to one aspect of the disclosure, a delivery catheter system comprises:
an anchor catheter;
a collapsible and expandable anchor for anchoring a prosthetic heart valve in a native heart valve, the anchor configured to be received within the anchor catheter;
a balloon catheter positioned radially inward of the anchor catheter, the balloon catheter including an inflatable balloon at a distal end thereof, the balloon being in fluid communication with the balloon catheter; and
a needle positioned radially inward of the balloon catheter and translatable relative to the balloon, the needle having a sharp distal tip; and/or
the balloon has an inflated condition and a deflated condition, the balloon having a tapered distal tip in the inflated condition; and/or
the needle is solid; and/or
the needle is hollow; and/or
the anchor catheter is steerable; and/or
a port catheter positioned radially outward of the anchor catheter, the anchor catheter being translatable relative to the port catheter; and/or
the port catheter is steerable; and/or
the anchor includes a tether having a first end fixedly attached to the anchor, and a second end opposite the first end, the second end configured to couple to the prosthetic heart valve; and/or
the balloon catheter is translatable relative to the anchor catheter.

According to another aspect of the disclosure, a method of delivering an expandable prosthetic heart valve anchor to a heart of a patient comprises:
positioning the anchor within an anchor catheter, the anchor catheter maintaining the anchor in a collapsed condition;
advancing the anchor catheter to a right atrium of the heart of the patient, through a puncture in an atrial septum of the heart of the patient, and into a left atrium of the heart of the patient;
advancing the anchor catheter from the left atrium of the heart of the patient to a left ventricle of the heart of the patient;
advancing a needle positioned radially within the anchor catheter distally relative to the anchor catheter and through a ventricular wall of the heart of the patient to create a transapical puncture;
advancing the anchor catheter at least partially through the transapical puncture; and
releasing the anchor from the anchor catheter and allowing the anchor to transition from the collapsed condition to an expanded condition while the anchor catheter is positioned at least partially through the transapical puncture; and/or
while the anchor catheter is positioned within the right atrium of the heart of the patient, advancing the needle distally through the atrial septum to create the puncture in the atrial septum; and/or a balloon catheter is positioned radially inward of the anchor catheter, the balloon catheter including an inflatable balloon at a distal end thereof, the balloon being in fluid communication with the balloon catheter; and/or the balloon has an inflated condition and a deflated condition, the balloon being tapered toward a distal end when in the inflated condition; and/or the balloon has an inflated condition and a deflated condition, the balloon being in the inflated condition while the needle is advanced through the ventricular wall of the heart of the patient; and/or deflating the balloon after the needle is advanced through the ventricular wall and before the anchor catheter is at least partially advanced through the transapical puncture; and/or advancing the deflated balloon at least partially through the transapical puncture before the anchor catheter is at least partially advanced through the transapical puncture; and/or inflating the balloon to dilate the transapical puncture after the deflated balloon is positioned at least partially within the transapical puncture; and/or the anchor catheter is positioned radially within a port catheter while the anchor catheter is positioned within the left atrium of the heart of the patient; and/or steering the port catheter while the port catheter is positioned within the left atrium of the heart of the patient so that a distal end of the port catheter is substantially aligned with a central longitudinal axis passing through an annulus of a native mitral valve of the patient; and/or translating the anchor catheter distally relative to the port catheter and through the annulus of the native mitral valve of the patient while the port catheter is substantially aligned with the central longitudinal axis passing through the annulus of the native mitral valve of the patient.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of delivering an expandable prosthetic heart valve anchor to a heart of a patient, the method comprising:
    positioning the anchor within an anchor catheter, the anchor catheter maintaining the anchor in a collapsed condition;
    advancing the anchor catheter to a right atrium of the heart of the patient, through a puncture in an atrial septum of the heart of the patient, and into a left atrium of the heart of the patient;
    advancing the anchor catheter from the left atrium of the heart of the patient to a left ventricle of the heart of the patient;
    advancing a needle positioned radially within the anchor catheter distally relative to the anchor catheter and through a ventricular wall of the heart of the patient to create a transapical puncture;
    advancing the anchor catheter at least partially through the transapical puncture; and
    releasing the anchor from the anchor catheter and allowing the anchor to transition from the collapsed condition to an expanded condition while the anchor catheter is positioned at least partially through the transapical puncture,
    wherein a balloon catheter is positioned radially inward of the anchor catheter, the balloon catheter including an inflatable balloon at a distal end thereof, the balloon being in fluid communication with the balloon catheter,
    wherein the balloon has an inflated condition and a deflated condition, the balloon being in the inflated condition while the needle is advanced through the ventricular wall of the heart of the patient.

2. The method of claim 1, further comprising:
    while the anchor catheter is positioned within the right atrium of the heart of the patient, advancing the needle distally through the atrial septum to create the puncture in the atrial septum.

3. The method of claim 1, wherein the balloon is tapered toward a distal end when in the inflated condition.

4. The method of claim 1, further comprising deflating the balloon after the needle is advanced through the ventricular wall and before the anchor catheter is at least partially advanced through the transapical puncture.

5. The method of claim 4, further comprising advancing the deflated balloon at least partially through the transapical puncture before the anchor catheter is at least partially advanced through the transapical puncture.

6. The method of claim 5, further comprising inflating the balloon to dilate the transapical puncture after the deflated balloon is positioned at least partially within the transapical puncture.

7. The method of claim 1, wherein the anchor catheter is positioned radially within a port catheter while the anchor catheter is positioned within the left atrium of the heart of the patient.

8. The method of claim 7, further comprising steering the port catheter while the port catheter is positioned within the left atrium of the heart of the patient so that a distal end of the port catheter is substantially aligned with a central longitudinal axis passing through an annulus of a native mitral valve of the patient.

9. The method of claim 8, further comprising translating the anchor catheter distally relative to the port catheter and through the annulus of the native mitral valve of the patient while the port catheter is substantially aligned with the central longitudinal axis passing through the annulus of the native mitral valve of the patient.

* * * * *